United States Patent [19]

Fujioka et al.

[11] Patent Number: 4,519,943
[45] Date of Patent: May 28, 1985

[54] 5-ALKOXYBICYCLO[2.2.1]HEPTANE-2-OXY-PROPANE DERIVATIVES AND USES THEREOF IN AUGMENTING OR ENHANCING THE AROMAS OF PERFUME COMPOSITIONS, COLOGNES AND PERFUMED ARTICLES

[75] Inventors: Futoshi Fujioka, Wanamassa; Richard M. Boden, Ocean; William L. Schreiber, Jackson; Patrick Whelan, Matawan; Marie R. Hanna, Hazlet, all of N.J.

[73] Assignee: International Flavors & Fragrances Inc., New York, N.Y.

[21] Appl. No.: 535,794

[22] Filed: Sep. 26, 1983

[51] Int. Cl.³ .................... A61K 7/46; C07C 47/34; C07C 35/24
[52] U.S. Cl. .................... 252/522 R; 252/522 A; 252/8.6; 252/174.11; 568/444; 568/445; 568/665
[58] Field of Search ............ 252/522 R, 522 A, 8.6, 252/174.11; 568/445, 665, 444

[56] References Cited

U.S. PATENT DOCUMENTS 3,780,109 12/1973 Schleppnik .................... 252/522 R
4,367,158 1/1983 Sprecker .................... 252/522 R

OTHER PUBLICATIONS

Wagner et al., Synthetic Organic Chemistry, (1953), pp. 149, 282.

*Primary Examiner*—Anton H. Sutto
*Attorney, Agent, or Firm*—Arthur L. Liberman

[57] ABSTRACT

Described are 5-alkoxybicyclo[2.2.1]heptane-2-oxypropane derivatives defined according to the structure:

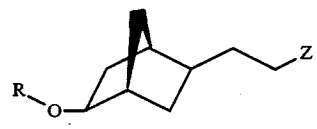

(wherein R represents $C_1$–$C_3$ alkyl and wherein Z represents one of the moieties, carbinol having the structure:

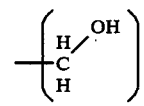

or carboxaldehyde having the structure:

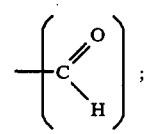

and uses thereof in augmenting or enhancing the aroma of perfume compositions, colognes or perfumed articles (e.g., solid or liquid anionic, cationic, nonionic or zwitterionic detergents, fabric softener compositions, fabric softener articles, cosmetic powders, hair preparations, perfumed polymers and the like).

21 Claims, 15 Drawing Figures

GLC PROFILE FOR EXAMPLE II. CRUDE

GLC PROFILE FOR EXAMPLE I. CRUDE

NMR SPECTRUM FOR EXAMPLE I.

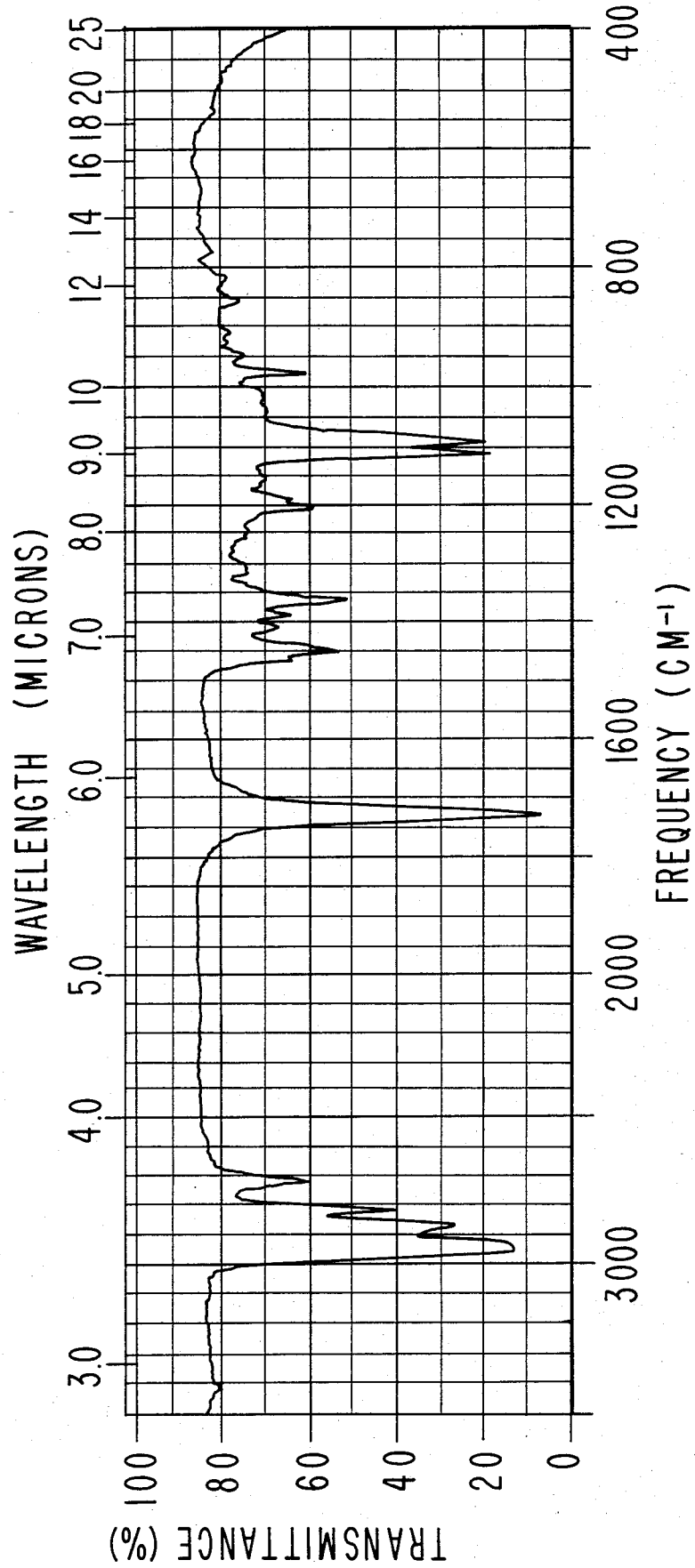

NMR SPECTRUM FOR FRACTION 8 OF EXAMPLE II.

IR SPECTRUM FOR FRACTION 8 OF EXAMPLE II.

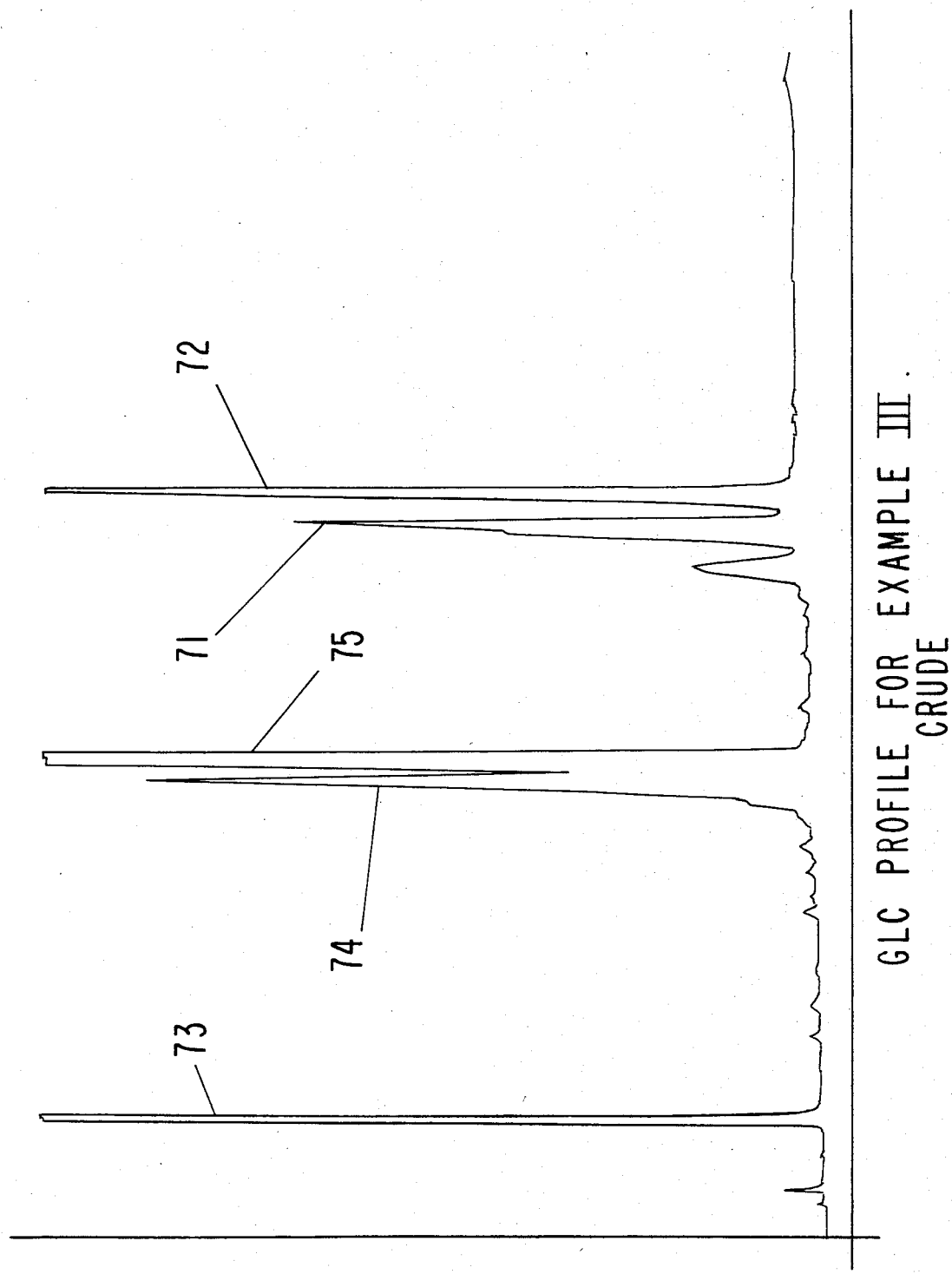

GLC PROFILE FOR FRACTION 10 OF EXAMPLE III. 2ND DISTILLATION.

GLC PROFILE FOR FRACTION 8 OF EXAMPLE III. 2ND DISTILLATION.

NMR SPECTRUM FOR FRACTION 10 OF EXAMPLE III.

FIG.11
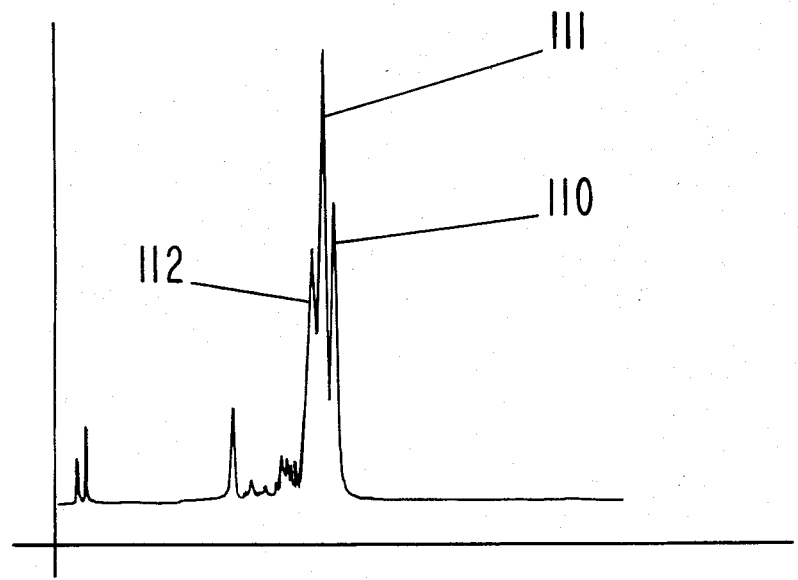
GLC PROFILE FOR EXAMPLE IV.
CRUDE
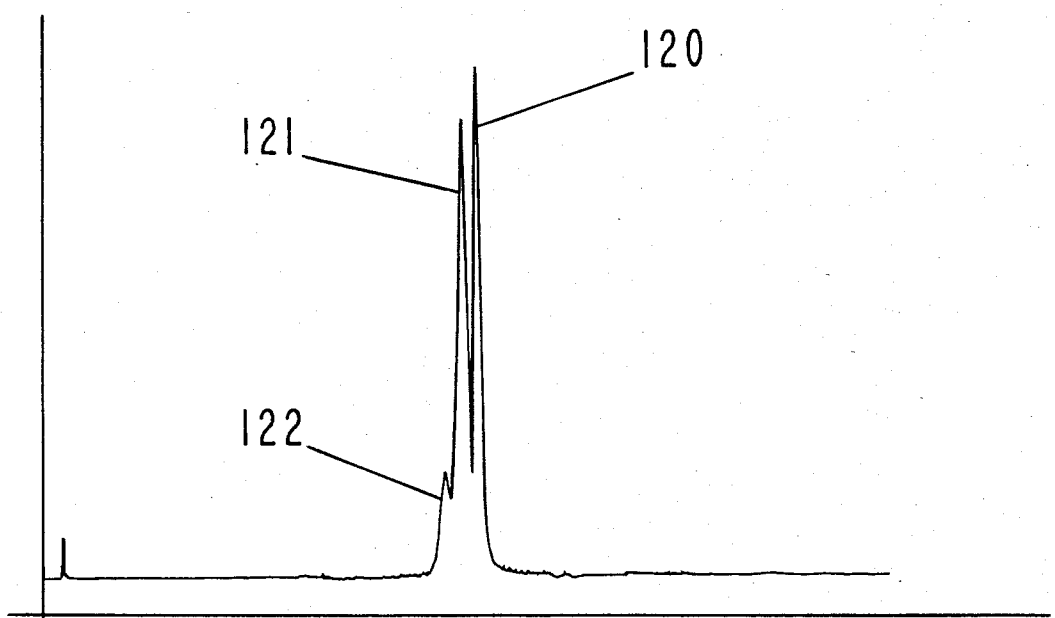
GLC PROFILE FOR FRACTION 5 OF EXAMPLE IV.
FIG.12

5-ALKOXYBICYCLO[2.2.1]HEPTANE-2-OXYPROPANE DERIVATIVES AND USES THEREOF IN AUGMENTING OR ENHANCING THE AROMAS OF PERFUME COMPOSITIONS, COLOGNES AND PERFUMED ARTICLES

BACKGROUND OF THE INVENTION

This invention relates to 5-alkoxybicyclo[2.2.1]heptane-2-oxypropane derivatives defined according to the structure:

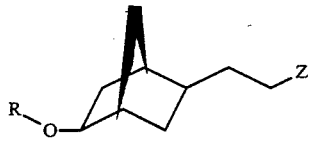

(wherein R represents $C_1$-$C_3$ alkyl and wherein Z represents one of the moieties, carbinol having the structure:

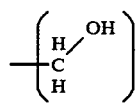

or carboxyaldehyde having the structure:

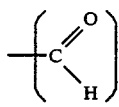

Inexpensive chemical compositions of matter which can provide balsamic, cedarwood, citrus, green, fruity, melony, orris and floral aromas are known and are highly desirable in practicing the art of perfumery. Many of the natural materials which provide such fragrances and contribute such desired nuances to perfumery compositions as well as perfumed articles (such as solid or liquid anionic, cationic, nonionic or zwitterionic detergents, fabric softener compositions, fabric softener articles and perfumed polymers) are high in cost, vary in quality from one batch to another and/or are generally subject to the usual variations of natural products.

Oxo reaction products are well known in the art of perfumery. Thus, U.S. Pat. No. 4,374,277 issued on Feb. 15, 1983, the specification of which is incorporated by reference herein describes branched chain $C_{11}$ aldehydes and alcohols, processes for producing same by (i) first dimerizing isoamylene (2-methyl-2-butene) to form a mixture of diisoamylenes and (ii) reacting the resulting mixture or separated components thereof with carbon monoxide and hydrogen by means of an oxo reaction, as well as methods for augmenting or enhancing the aroma of perfumes, colognes and perfumed articles by adding thereto aroma augmenting or enhancing quantities of the thus produced $C_{11}$ branched chain aldehydes and alcohol compositions of matter.

Furthermore, ether carboxaldehydes are well known in the art of perfumery for augmenting or enhancing the aroma of perfume compositions or perfumed articles. Thus, U.S. Pat. No. 4,359,390 issued on Nov. 16, 1982, the specification for which is incorporated by reference herein discloses the use of such ether carboxaldehydes as the compound having the structure:

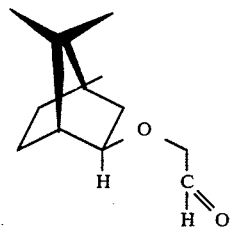

in augmenting or enhancing the aroma of perfume compositions, colognes and perfumed articles (e.g., perfume plastics, solid or liquid anionic, cationic, nonionic or zwitterionic detergents, fabric softener compositions or drier-added fabric softener articles.

Nothing in the prior art however, suggest the 5-alkoxybicyclo[2.2.1]-heptane-2-oxopropane derivatives of our invention, or the organoleptic uses of same.

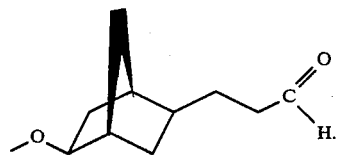

Figure 2:
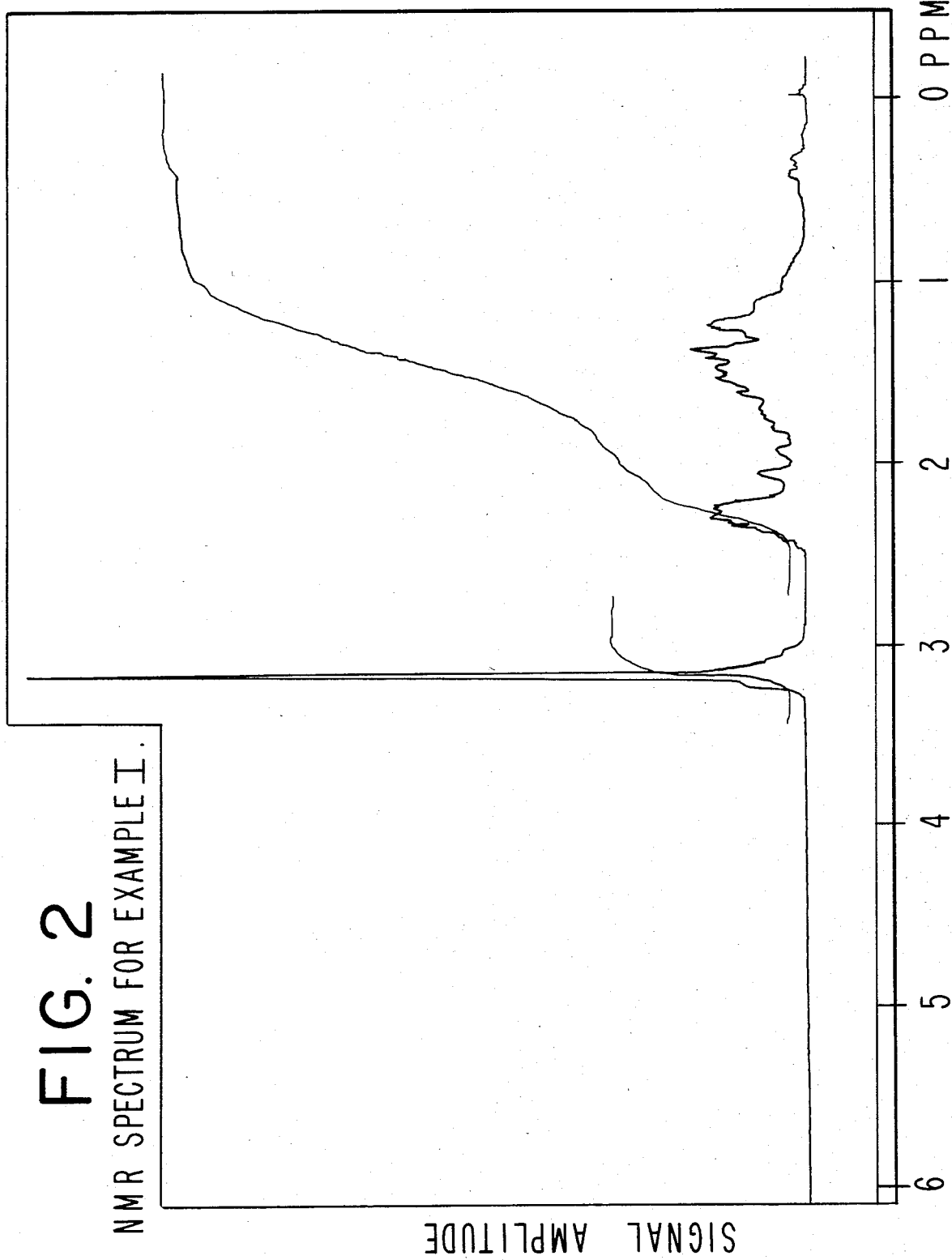

FIG. 2 is the NMR spectrum for a mixture of compounds having the structures:

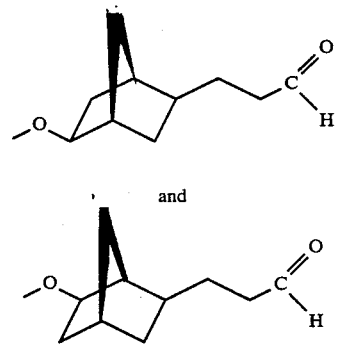

produced according to Example I. (Conditions: Field strength; 100 MHz; Solvent: $CFCl_3$).

FIG. 3 is the infra-red spectrum for the compound having the structure:

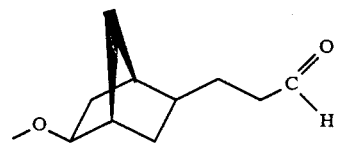

produced according to Example I.

Figure 4:
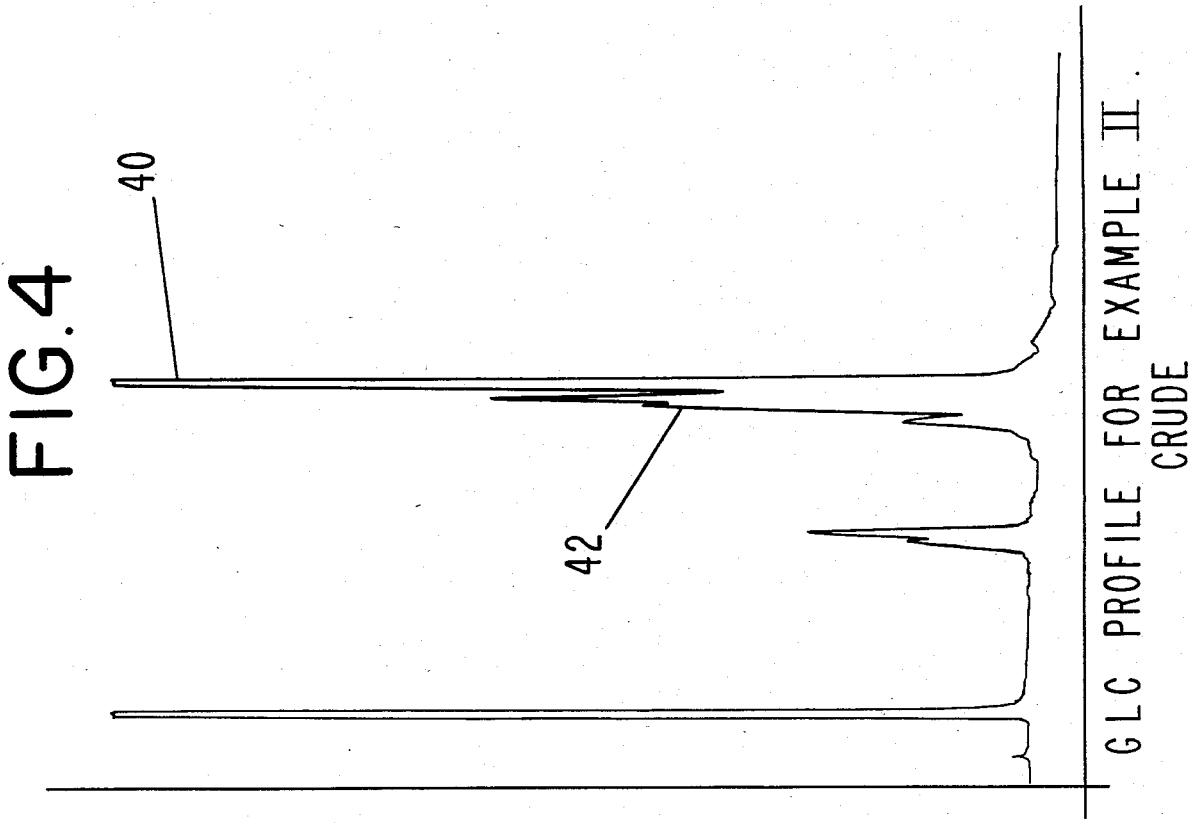

FIG. 4 is the GLC profile for the crude reaction product of Example II containing the compound having the structure:

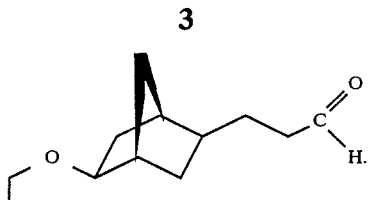

Figure 5:
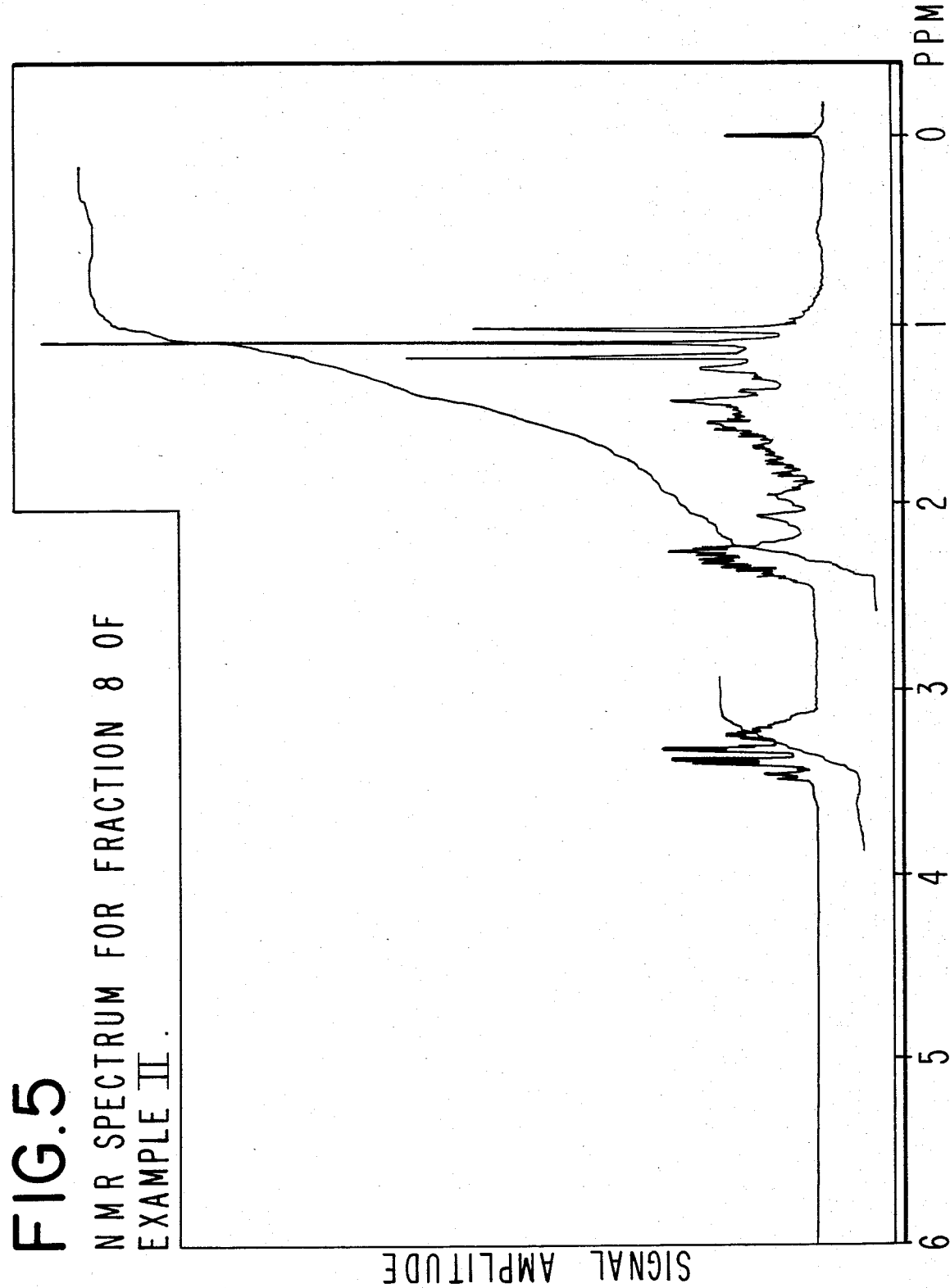

FIG. 5 is the NMR spectrum for Fraction 8 of the distillation product of the reaction product of Example II containing the compound having the structure:

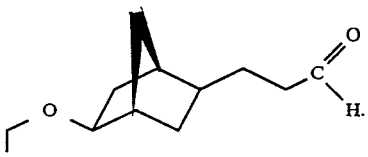

Figure 6:
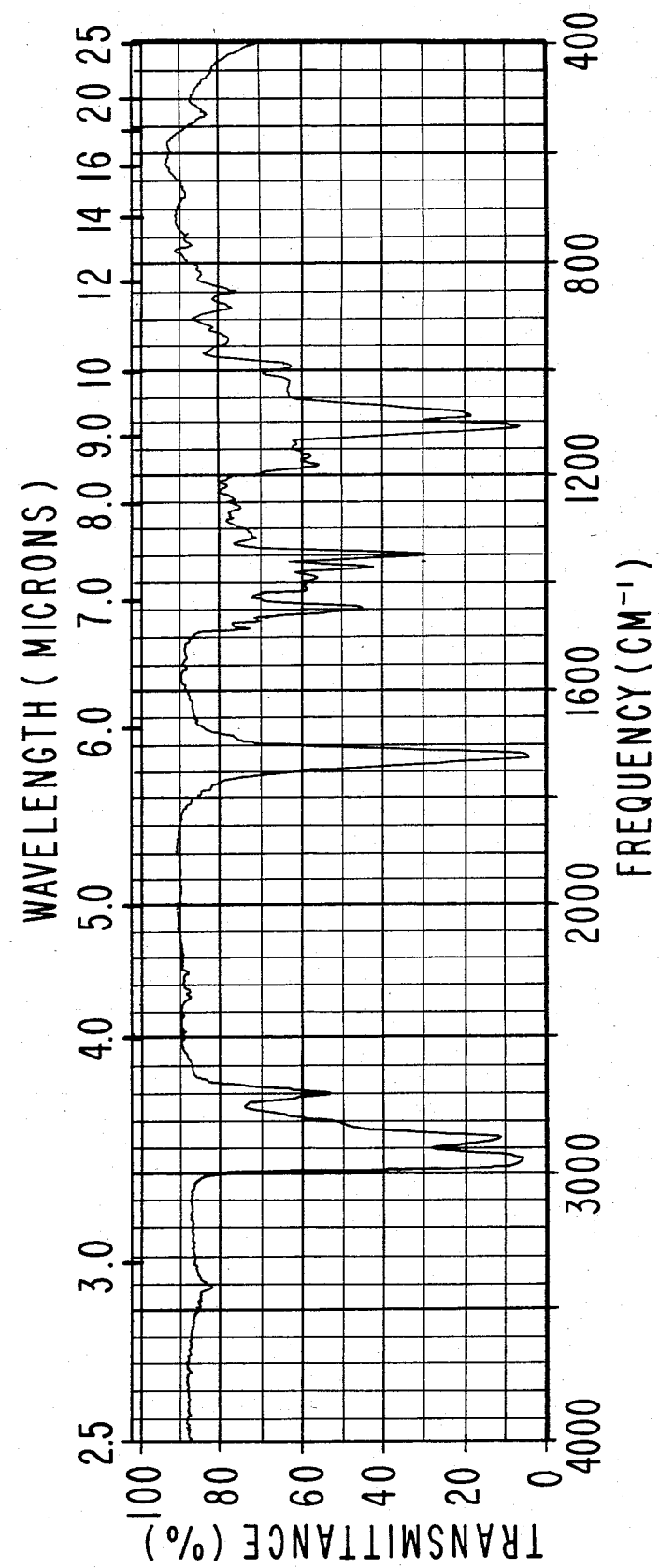

FIG. 6 is the infra-red spectrum for Fraction 8 of the distillation product of the reaction product of Example II containing the compound having the structure:

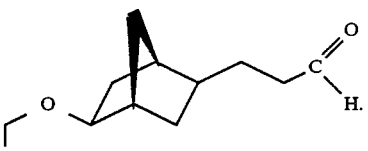

FIG. 7 is the GLC profile for the crude reaction product of Example III containing the compound having the structure:

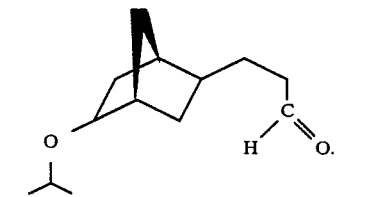

Figure 8:
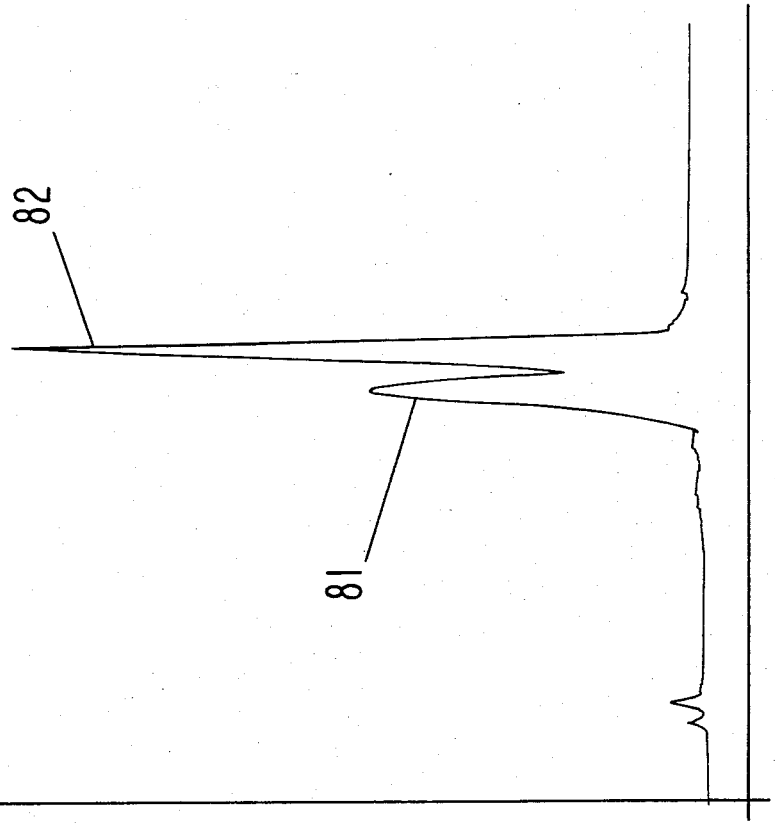

FIG. 8 is the GLC profile for Fraction 8 of the second distillation product of the reaction product of Example III containing the compound having the structure:

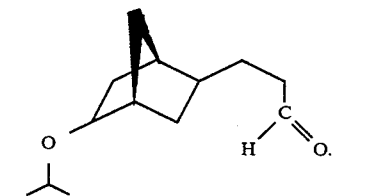

Figure 9:
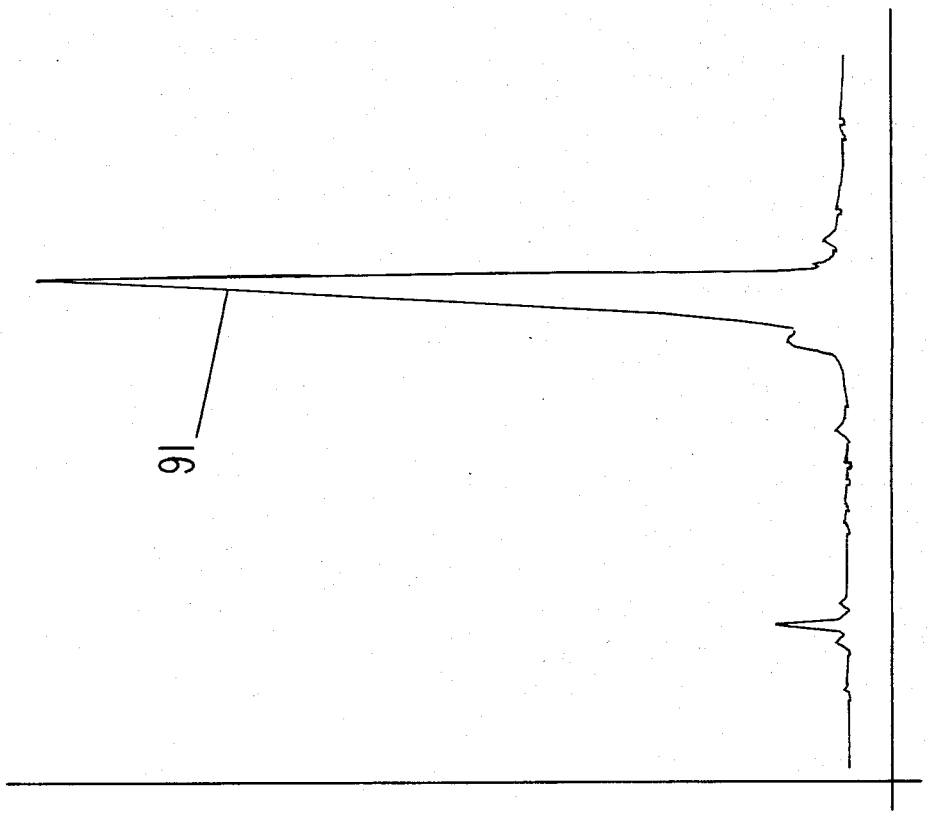

FIG. 9 is the GLC profile for Fraction 10 of the second distillation product of the reaction product of Example III containing the compound having the structure:

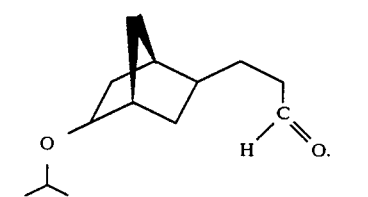

Figure 10:
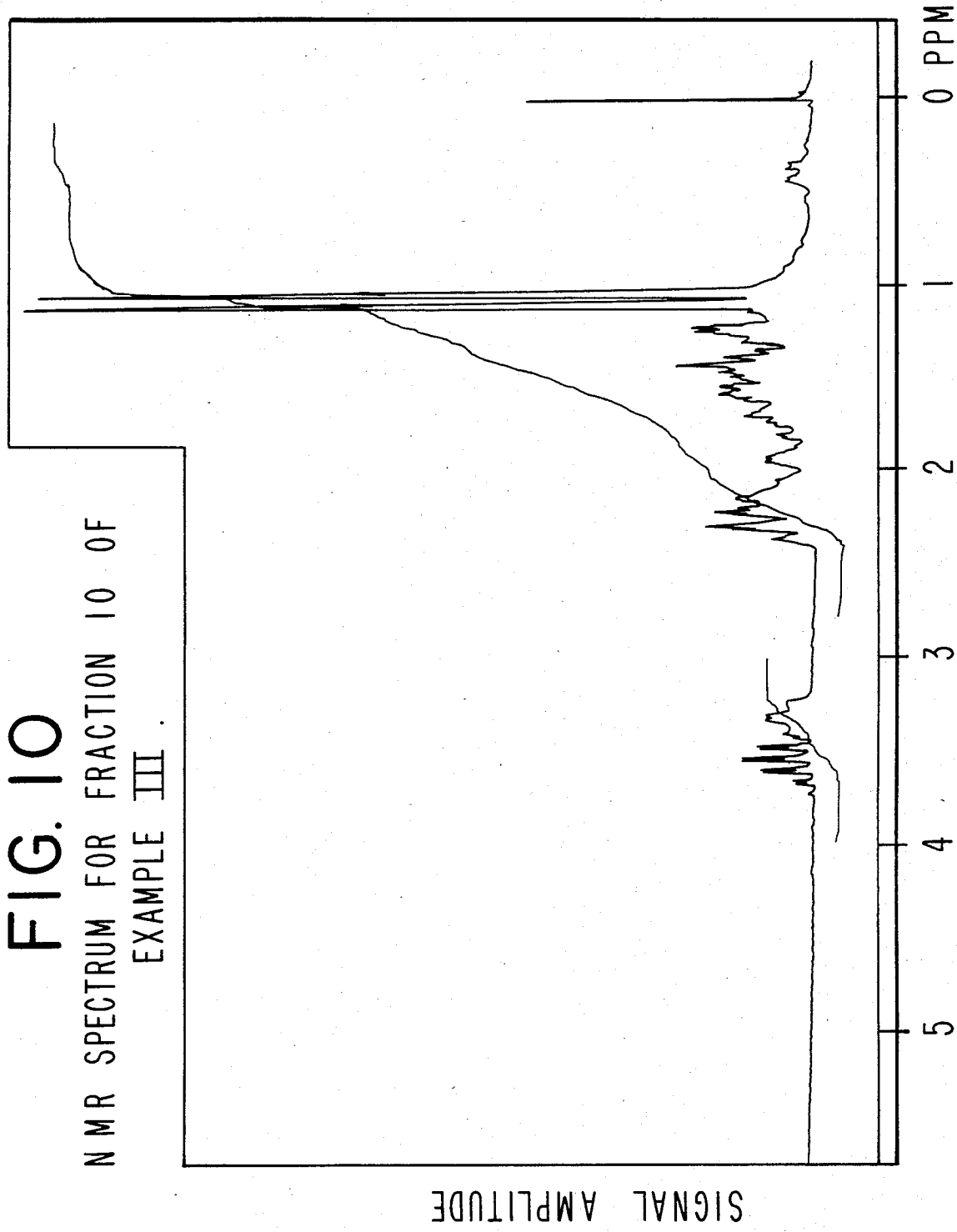

FIG. 10 is the NMR spectrum for Fraction 10 of the distillation product of the reaction product of Example III containing the compound having the structure:

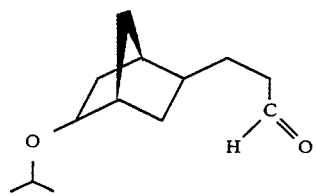

(Conditions: Field strenght: 100 MHz; Solvent: CFCl₃).

FIG. 11 is the GLC profile for the crude reaction product of Example IV containing the compound having the structure:

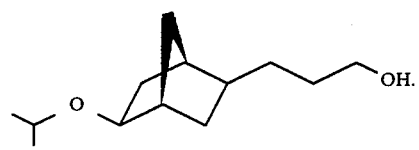

FIG. 12 is the GLC profile for Fraction 5 of the distillation product of the reaction product of Example IV containing the compound having the structure:

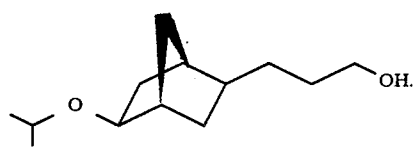

Figure 13:
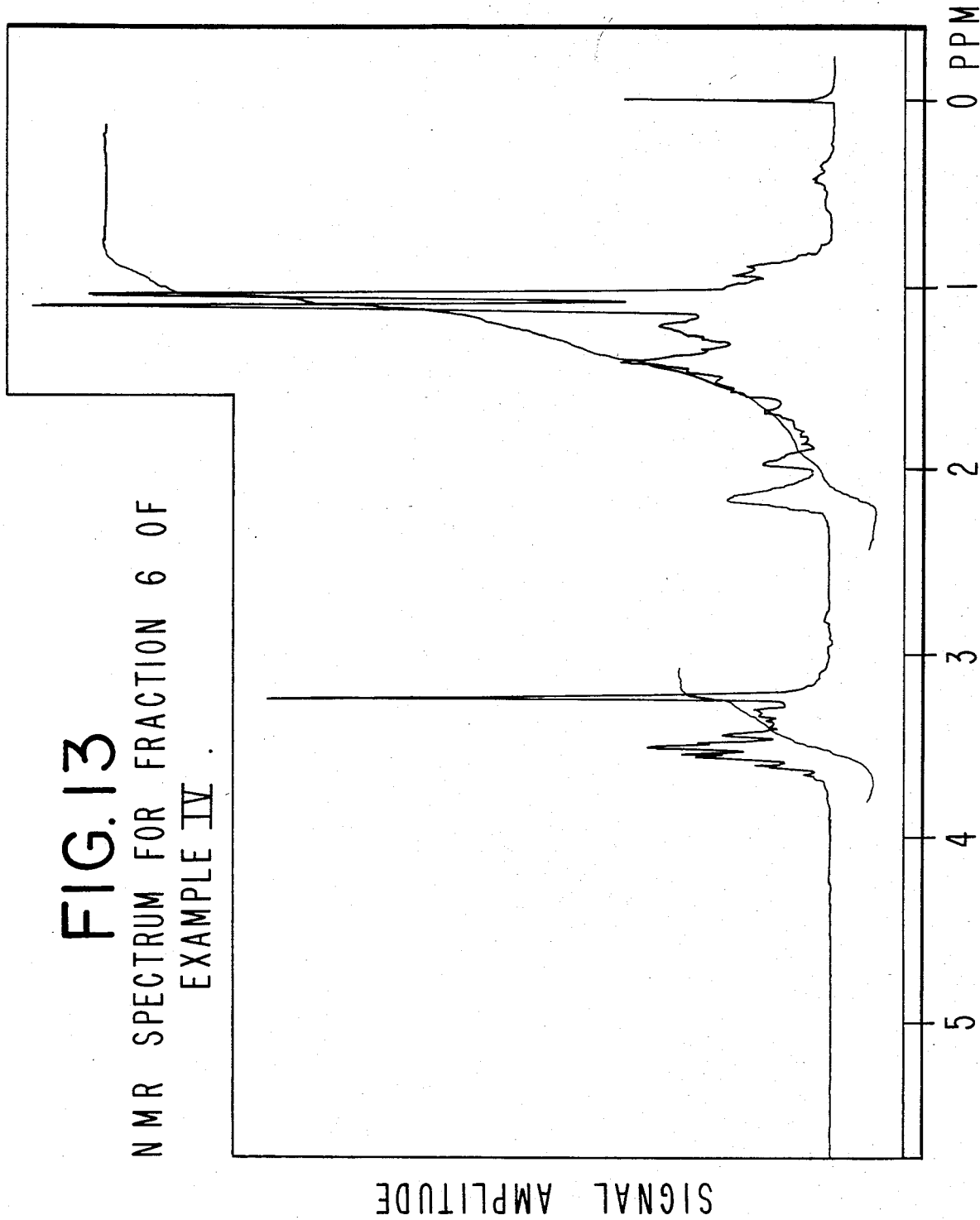

FIG. 13 is the NMR spectrum for Fraction 6 of the distillation product of the reaction product of Example IV containing the compound having the structure:

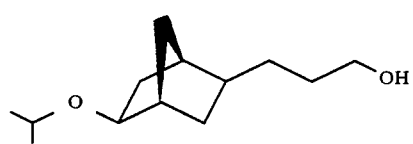

(Conditions: Field strength: 100 MHz; Solvent: CFCl₃).

Figures 14, 15:
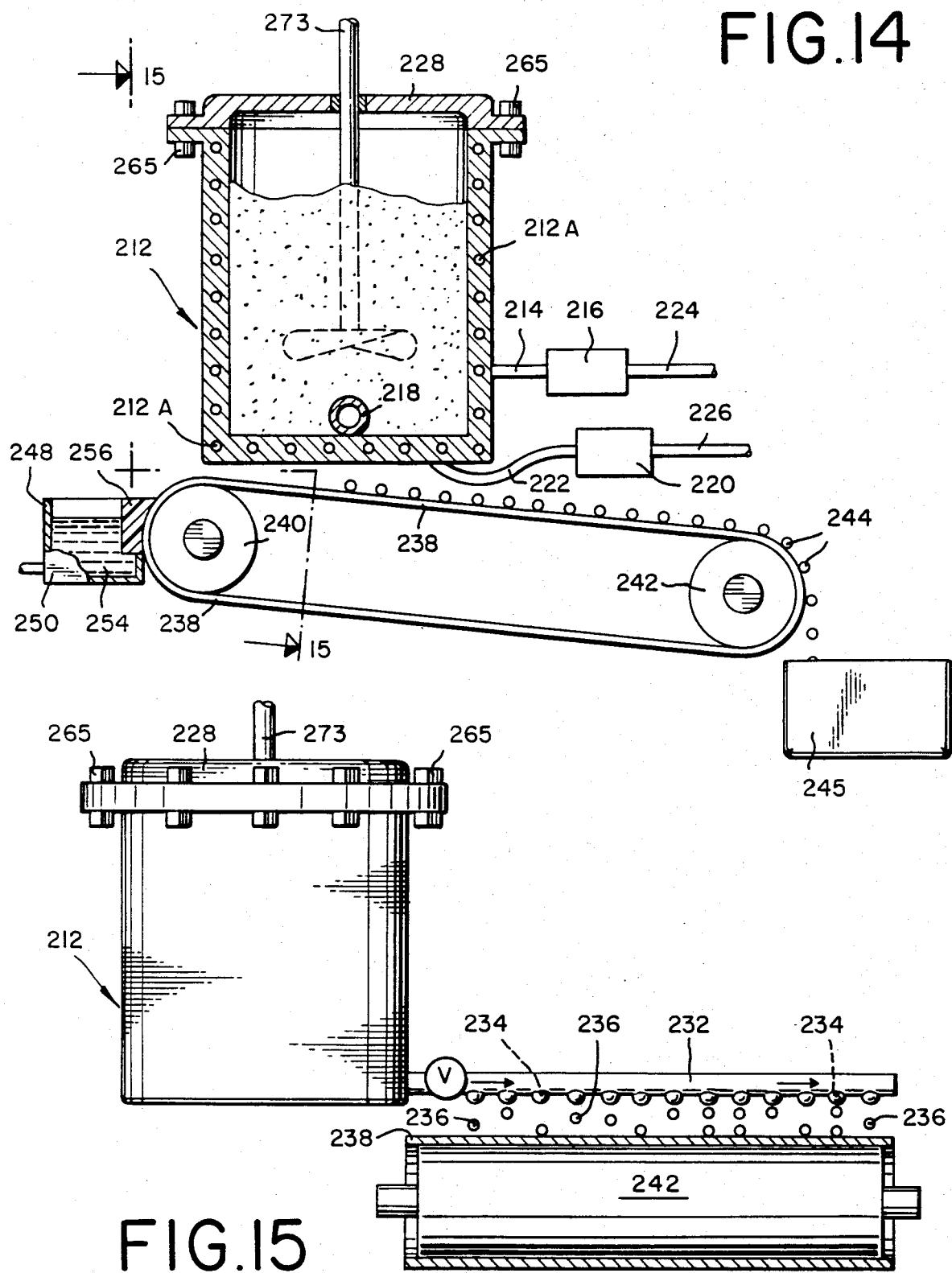

FIG. 14 represents a cut-away side elevation view of apparatus used in forming perfumed polymers which contain imbedded therein at least one of the 5-alkoxybicyclo[2.2.1]heptane-2-oxypropane derivatives of our invention.

FIG. 15 is a front view of the apparatus of FIG. 14 looking in the direction of the arrows.

DETAILED DESCRIPTION OF THE DRAWINGS

Figure 1:
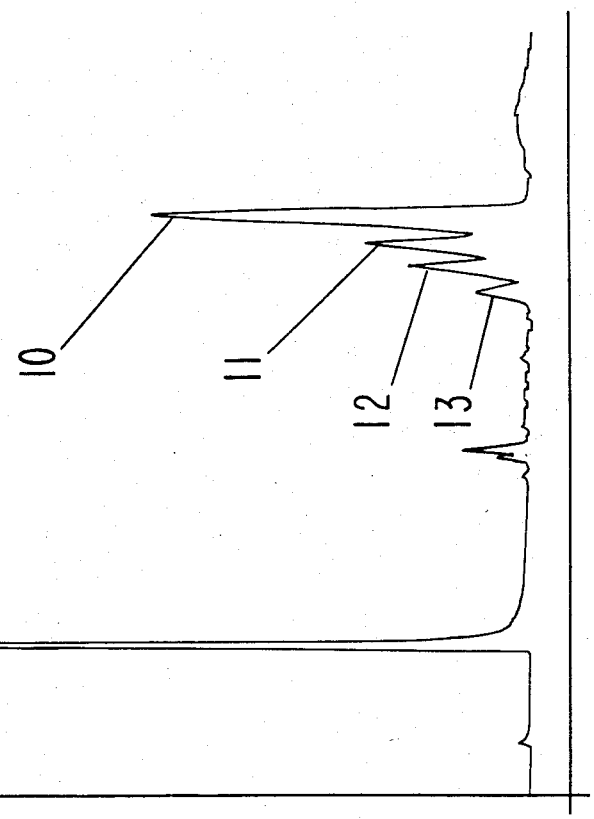
FIG. 1 is the GLC profile for the crude reaction product of Example I containing the compound having the structure.

FIG. 1 is the GLC profile of the crude reaction product of Example I. The major peak indicated by reference numeral "10" is the peak for the compound having the structure:

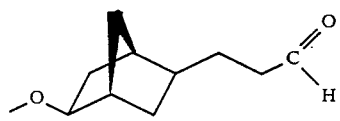

Minor peaks "11", "12" and "13" are indicative of other materials in the reaction product including the isomer having the structure:

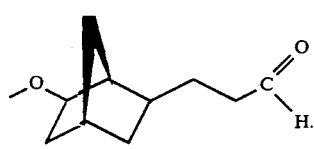

FIG. 4 is the GLC profile for the crude reaction product of Example II. The major proportion of that crude reaction product is a compound defined according to the structure:

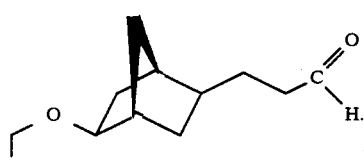

The peak indicated by reference numeral "40" is the peak for the compound having the structure:

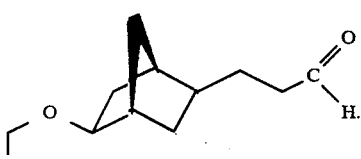

The mixture also contains the compound having the structure:

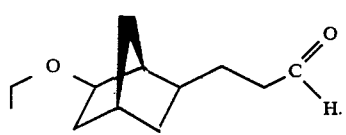

The peak indicated by reference numeral "42" is a peak which includes the compound having the structure:

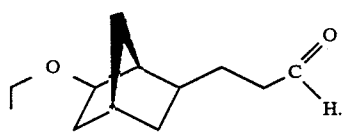

The NMR spectrum of FIG. 5 which is for Fraction 8 of the distillation product of the reaction product of Example II is for a mixture which contains a major proportion of the compound having the structure:

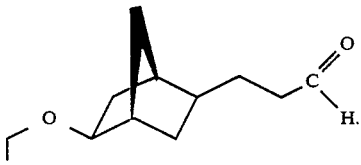

That mixture also contains in a minor proportion the compound having the structure:

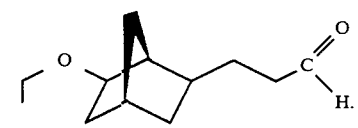

FIG. 7 is the GLC profile for the crude reaction product of Example III. The peak indicated by reference numeral "72" is the peak for the reaction product having the structure:

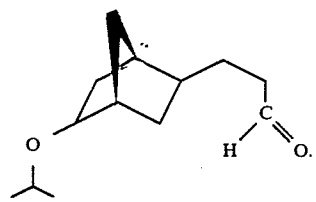

The peak indicated by reference numeral "73" is the peak for the starting material defined according to the structure:

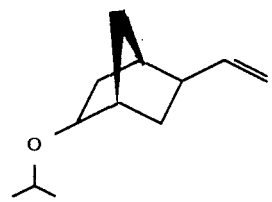

Other isomers of the reaction product are indicated by the peak indicated by reference numeral "71". The compounds included in the peak indicated by reference numeral "17" include the compound defined according to the structure:

The compounds having the structures:

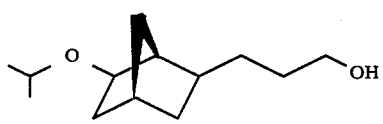

and

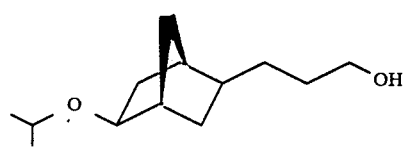

are also present in the peaks indicated by reference numeral "71" "74" and "75".

FIG. 8 is a GLC profile for Fraction 8 of the second distillation product of the reaction product of Example III. The peak indicated by reference numeral "82" is the peak for the compound having the structure:

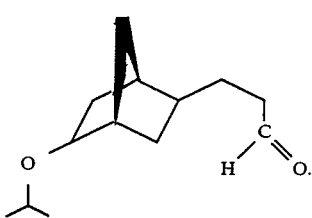

The peak indicated by reference numeral "81" is the peak for the compound having the structure:

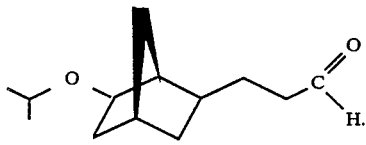

FIG. 9 is the GLC profile for Fraction 10 of the second distillation product of the reaction product of Example III. The peak indicated by reference numeral "91" is the peak for the compound having the structure:

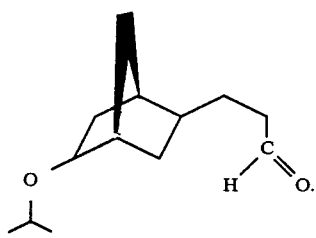

FIG. 11 is the GLC profile for the crude reaction product of Example IV. The peaks indicated by reference numerals "110", "111" and "112" are peaks for the reaction product which have the structures:

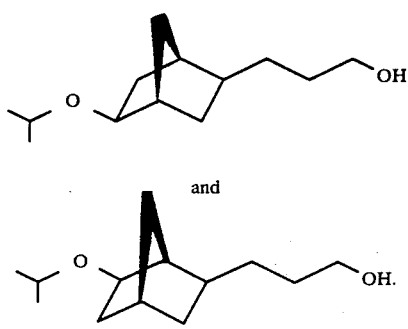

and

FIG. 12 is the GLC profile for Fraction 5 of the distillation product of the reaction product of Example IV. The peaks indicated by reference numerals "120", "121" and "122" are peaks for the compounds having the structures:

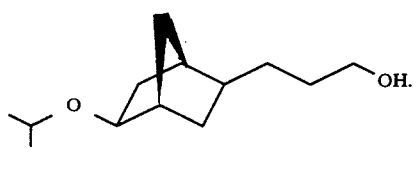

and

-continued

The compound having the structure:

is the compound which is in a major proportion in the resulting mixture.

Referring to FIGS. 14 and 15, there is provided a process for forming scented polymer elements (wherein the polymer may be a thermoplastic polymers such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 23 and 24, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the 5-alkoxybicyclo[2.2.1]heptane-2-oxypropane derivatives of our invention or mixtures of 5-alkoxybicyclo[2.2.1]-heptane-2-oxypropane derivatives of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212A having heating coils which are supplied with electric current through cable 214 from a rheostate or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the 5-alkoxybicyclo[2.2.1]heptane-2-oxypropane derivatives of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the 5-alkoxybicyclo[2.2.1]heptane-2-oxypropane derivatives of our invention or mixture of 5-alkoxybicyclo[2.2.1]heptane-2-oxypropane derivatives with another perfume substance will continuously drop through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume which is all of, or which contains one or more of the 5-alkoxybicyclo[2.2.1]heptane-2-oxypropane derivatives of our invention, through the orifices 234 at a rate which will insure the formation of droplets 236 which will fall downwardly onto a moving conveyor belt 238 caused to run between the conveyor wheels 240 and 242 beneath the conduit 232.

When the droplets 236 fall onto the conveyor 238, they form pellets 244 which harden almost instantaneously and fall off the end of the conveyors 238 into a container 250 which is advantageously filled with water or some other suitable cooling liquid in which the polymer and perfume is insoluable, to insure the rapid cooling of each of the pellets 244. The pellets 244 are then collected from the container 250 and utilized for the formation of other functional products, e.g., garbage bags and the like.

THE INVENTION

The present invention provides compounds defined according to the genus:

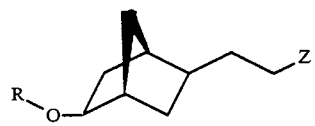

(wherein R represents $C_1$-$C_3$ alkyl and wherein Z represents one of the moieties, carbinol having the structure:

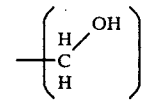

or carboxaldehyde having the structure:

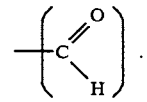

The present invention also provides for a process for preparing such compounds by means of carrying out an oxo reaction on alkyl norbornyl vinyl substituted ethers having the generic structure:

wherein R is $C_1$-$C_3$ alkyl according to the reaction:

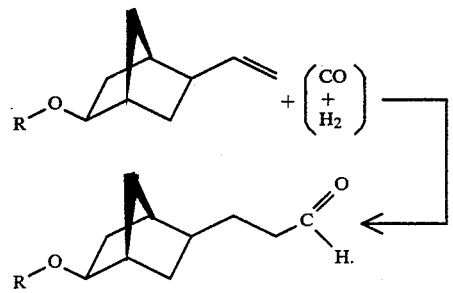

The resulting aldehydes defined according to the structure:

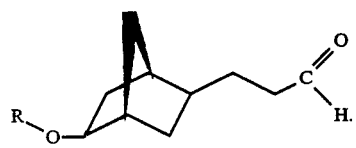

may, if desired, be further reduced using a reducing agent to form the corresponding alcohol having the structure:

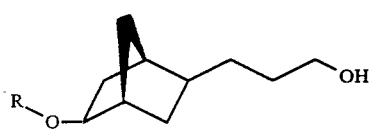

according to the reaction:

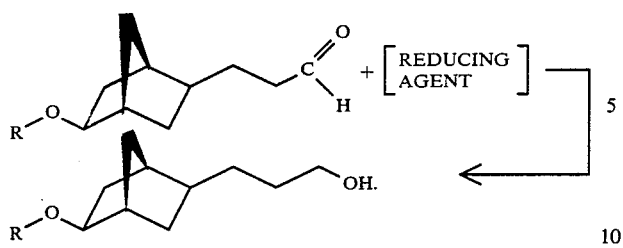

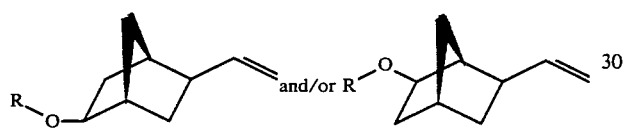

The 5-alkoxybicyclo[2.2.1]heptane-2-oxypropane derivatives of our invention as well as mixtures thereof produced according to the process of our invention are capable of modifying or enhancing the aroma characteristics of perfume compositions, colognes and perfumed articles (including soaps, anionic, cationic, non-ionic or zwitterionic detergents, fabric softener compositions, fabric softener articles, optical brightener compositions and perfumed polymers) by imparting thereto balsamic, cedarwood, citrus and fragrance nuances, thus fulfilling a need in the field of perfumery and detergent and cosmetic manufacture.

As stated, supra, the 5-alkoxybicyclo[2.2.1]heptane-2-oxypropane derivatives of our invention are prepared by first reacting one or more alkoxy vinyl ethers having one of the structures:

with a mixture of carbon monoxide and hydrogen (thereby carrying out an "oxo" reaction) in the presence of a "oxo" reaction catalyst. The mole ratio of carbon monoxide and hydrogen may vary from about 1:0.1 up to about 0.1:1 (mole:mole of carbon monoxide:hydrogen) with a preferred mole ratio of carbon monoxide:hydrogen being about 1:1. The oxo reaction is carried out at temperature of between 150° C. and 300° C.; at pressures of between 20 250 atmospheres; with, as stated, supra, the ratio of partial pressure of carbon monoxide:hydrogen being from 0.1:1 up to 1:0.1.

Any oxo type reaction catalyst may be used but most preferably, the catalyst yielding the best perfume mixtures are as follows:
Dicobalt octacarbonyl;
Cobalt octanoate;
Palladium chloride;
Rhodium trichloride;
Iron pentacarbonyl;
Nickel tetracarbonyl;
Polymer-bonded rhodium catalyst (e.g., rhodium bonded on a polystyrene substrate);
Tris-triphenyl phosphine rhodium-1-chloride;
Rhodium Aceto acetate dicarbonyl;
Rhodium Aceto acetate/triphenyl phospine mixture.
The reaction time may vary from about 2 hours up to about 30 hours; and the reaction time is a function of the temperature and pressure of reaction. At the end of the reaction, the reaction product is separated from the catalyst and the unreacted materials by standard "work-up" means; e.g., neutralization of catalyst; followed by extraction and fractional distillation; usually an initial functional distillation by means of distillation through a 3 or 4 plate or stone packed column; followed by a more careful fractionation of the bulked center-cut fractions on, for example, a spinning band column or multi-plate (14–50 plate) fractionation column. The materials may then be further separated as by means of commercial chromatographic separations e.g., HPLC techniques well known in the art.

The resulting products defined according to the structures:

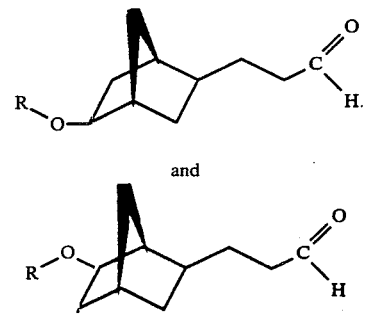

and depending upon whether the starting material has the structure:

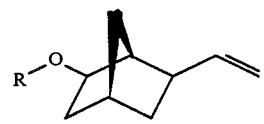

or the structure:

(wherein R represents $C_1$–$C_3$ lower alkyl) may then be further reduced using a reducing agent, for example:
Sodium borohydride;
Potassium borohydride;
Lithium borohydride; or
Lithium alumunium hydride
according to the general reaction:

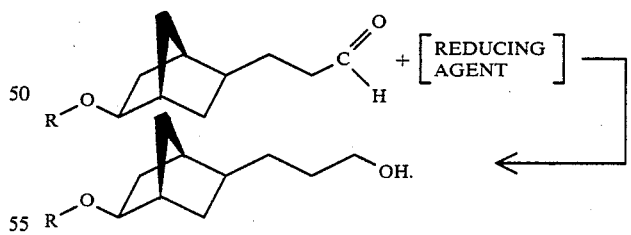

Usually, the commerically available alkoxy vinyl norbornene contains a major proportion of compound having the structure:

(60–80%) and a minor proportion of compound having the structure:

(20–40%).

Accordingly, as a general rule the 5-alkoxybicyclo[2.2.1]-heptane-2-oxypropane derivatives of our invention may be written thusly:

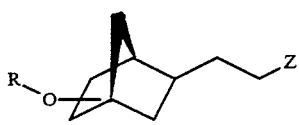

(wherein R represents $C_1$–$C_3$ alkyl and wherein Z represents one of the moieties, carbinol having the structure:

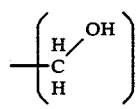

or carboxaldehyde having the structure:

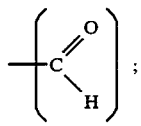

in order to show a mixture of the genus of compounds defined according to the structure:

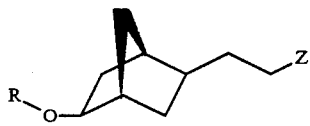

as well as the genus of compounds defined according to the structure:

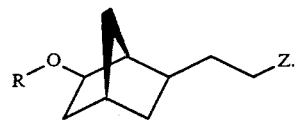

Furthermore, the reduction reaction, to wit:

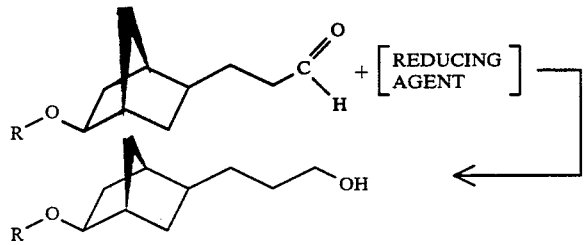

is carried out in the presence of an inert solvent such as isopropyl alcohol, n-butanoyl or ethyl alcohol at reflux conditions for a period of time of between about 2 hours and about 10 hours. At the end of the reaction, the reaction mass is neutralized (in order to remove the effect of the catalyst) and the reaction mass is then distilled in order to purify the resultant compound and utilize same for its organoleptic properties. If desired, the resultant mixture may be separated into various components by means of chromatographic techniques, e.g., HPLC.

Examples of the 5-alkoxybicyclo[2.2.1]heptane-2-oxypropane derivatives of our invention and their organoleptic properties are as follows:

TABLE I

| Structure | Perfume Properties |
|---|---|
| Mixture of compounds having the structures: | A highly intense, balsamic aroma reminescent of natural peru balsom. |
| Mixture of compounds having the structures: | A balsamic, cedarwood-like, citrusy and floral aroma profile. |
| Mixture of compounds having the structures: | A green, aldehydic aroma with a fatty, orris note and slight melony, woody (twiggy) undertones. |
| Mixture of compounds having the structures: | A green, fruity, meloney, aldehydic and slightly woody aroma profile. |

TABLE I-continued

| Structure | Perfume Properties |
|---|---|
|  | |

One or more of the 5-alkoxybicyclo[2.2.1]heptane-2-oxypropane derivatives of our invention prepared in accordance with the process of our invention and one or more auxiliary perfume ingredients including, for example, alcohols, other than the 5-alkoxybicyclo[2.2.1]heptane-2-oxypropane derivatives of our invention, aldehydes other than the 5-alkoxybicyclo[2.2.1]heptane-2-oxypropane derivatives of our invention, ketones, terpinic hydrocarbons, nitriles, esters, lactones, natural essential oils, synthetic essential oils and mercaptans and mercapto ethers may be admixed so that the combined odors of the individual components produce a pleasant and desired fragrance, particularly and preferably, in the pine and floral fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions it is the individual components which contribute to their particular olfactory characteristics, however the overall sensory effect of the perfume composition will be at least the sum total of the effects of each of the ingredients. Thus, one or more 5-alkoxybicyclo[2.2.1]heptane-2-oxypropane derivatives prepared in accordance with the process of our invention can be used to alter, modify or enhance the aroma characteristics of a perfume composition, for example, by utilizing or moderating the olfactory reaction contributed by another ingredient in the composition.

The amount of one or more of the 5-alkoxybicyclo[2.2.1]heptane-2-oxypropane derivatives prepared in accordance with the process of our invention which will be effective in perfume compositions as well as in perfumed articles (e.g., anionic, nonionic, cationic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of one or more of the 5-alkoxybicyclo[2.2.1]heptane-2-oxypropane derivatives prepared in accordance with the process of our invention and less than 50% of one or more of the 5-alkoxybicyclo[2.2.1]heptane-2-oxypropane derivatives prepared in accordance with the process of our invention or even less (e.g., 0.005%) can be used to impart balsamic, cedarwood, citrus, green, fruity, melony, orris-like and floral aroma nuances to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on consideration of cost, nature of the end product, the effect desired on the finished product and the particular fragrance sought.

One or more of the 5-alkoxybicyclo[2.2.1]heptane-2-oxypropane derivatives prepared in accordance with the process of our invention is useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powder, face powders, and perfumed polymers and articles of manufacture produced from said perfumed polymers. When used as (an) olfactory component(s) as little as 0.2% of one or more of the 5-alkoxybicyclo[2.2.1]heptane-2-oxypropane derivatives prepared in accordance with the process of our invention will suffice to impart an intense balsamic, cedarwood-like, citrus green, fruity, melony, orris-like and floral fragrance nuances to floral or piney formulations. Generally, no more than 6% of one or more of the 5-alkoxybicyclo[2.2.1]heptane-2-oxypropane derivatives of our invention based on the ultimate end product is required in the perfumed article composition. Accordingly, the range of 5-alkoxybicyclo[2.2.1]heptane-2-oxypropane derivatives is from about 0.2% by weight of the 5-alkoxybicyclo[2.2.1]heptane-2-oxypropane derivatives up to about 6% by weight based on the weight of the perfumed article. In addition, the perfume composition or fragrance composition of our invention can contain a vehicle or carrier for one or more of the 5-alkoxybicyclo[2.2.1]heptane-2-oxypropane derivatives prepared in accordance with the process of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation or such as ureaformaldehyde polymer forming a capsule shell around a liquid perfume center).

Our invention also relates to the utilization of controlled release technology for the controlled release of perfumes into gaseous environments from polymers such as mixtures of epsilon polycaprolactone polymers and polyethylene which poly epsilon caprolactone polymers are defined according to at least one of the structures:

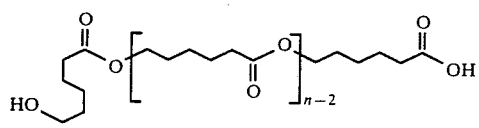

and/or

-continued

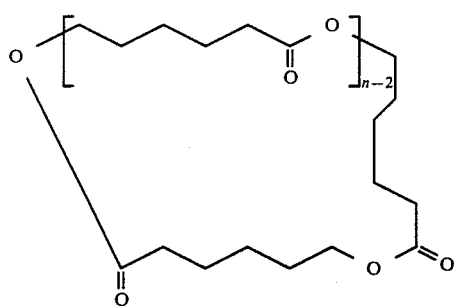

wherein "n" is from about 50 up to about 1,200 with the proviso that the average "n" in the system varies from about 150 up to about 700 according to the mathematical statement:

$$[700 \geq \bar{\eta} \geq 150]$$

with the term $\bar{\eta}$ being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$dM_t/dt = k_1 e^{-k_2 t}$$

wherein $K_1$ and $K_2$ are constants. According to Kydonieus, "Controlled Release Technologies: Methods, Theory, and Applications" (cited, supra), the amount of perfume composition released is proportional to time as long as the concentration of perfume material present, e.g., the 5-alkoxybicyclo[2.2.1]-heptane-2-oxypropane derivatives of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-dependent phenomenon, the release being constant (zero order) as long as the surface area does not change during the erosion process. This is the case with the polymers containing the 5-alkoxybicyclo[2.2.1]heptane-2-oxypropane derivatives of out invention.

The polyepsilon caprolactone polymers useful in practicing our invention are more specifically described in the brochure of the Union Carbide Corporation, 270 Park Avenue, New York, N.Y. 10017, entitled NEW POLYCAPROLACTONE THERMOPLASTIC POLYMERS PCL-300 AND PCL-700. These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone useful in conjunction with our invention against discoloration are dihydroxybenzenes such hydroquinone or compounds having the formula:

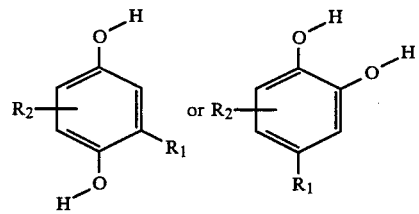

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfere with the functional fluids dissolved and/or adsorbed into the polymeric matrix.

The method of incorporating the 5-alkoxybicyclo[2.2.1]heptane-2-oxypropane derivatives of our invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylenepolyepsilon caprolactone polymer mixture (50:50) is mixed with one of the 5-alkoxybicyclo[2.2.1-]heptane-2-oxypropane derivatives of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700:polyethylene in molten form is admixed with a high percentage of one of the 5-alkoxybicyclo[2.2.1]heptane-2-oxypropane derivatives of our invention and the mixture is solidified in the form of pellets or beads. These pellets or beads thus contain a high percentage of the 5-alkoxybicyclo[2.2.1]heptane-2-oxypropane derivatives (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification 1,589,201 publlished on May 7, 1981, the specification for which is incorporated by reference herein.

In accordance with the present invention at least one of the 5-alkoxybicyclo[2.2.1]heptane-2-oxypropane derivatives of our invention is added to the polymer in a large closed container or drum which is maintained under controlled temperature conditions while the polymer in a melted condition is mixed with at least one of the 5-alkoxybicyclo[2.2.1]heptane-2-oxypropane derivatives of our invention under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one of the 5-alkoxybicyclo[2.2.1]heptane-2-oxypropane derivatives of our invention is permitted to drip through the orifices onto a continuously moving, cooled conveyor upon which the polymer containing at least one of the 5-alkoxybicyclo[2.2.1]heptane-2-oxypropane derivatives of our invention solidifies into small size pellets with the perfume imprisoned therein. The apparatus useful in conjunction with this process advantageously includes a conveyor of a material which will not adhere to the polymer which contains at least one of the 5-alkoxybicyclo[2.2.1]heptane-2-oxypropane derivatives of our invention.

In order that the droplets form into uniform pellets or beads, the conveyor is continuously washed with a liquid such as water to maintain the surface relatively cool. The pellets are delivered by the conveyor into a container and packaged for shipment.

The following Examples I–IV serve to illustrate processes for preparing the 5-alkoxybicyclo[2.2.1]heptane-2-oxypropane derivatives of our invention. The examples following Example IV are illustrative of the organoleptic utilities of the 5-alkoxybicyclo[2.2.1]heptane-2-oxypropane derivatives of our invention. All parts and percentages given herein are by weight unless otherwise specified.

EXAMPLE I

PREPARATION OF METHOXY NORBORNANBUTANAL (5-METHOXY-2-NORBORNANE-PROPANAL)

Reaction:

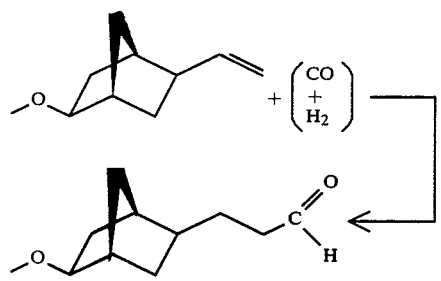

Into a 500 cc autoclave is placed 200 grams of a 60:40 (mole:mole) mixture of methoxy vinyl norbornenes having the structures:

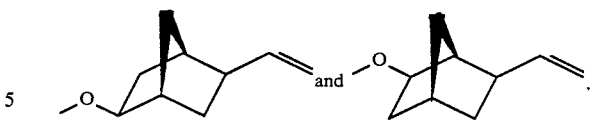

respectively, (1.32 moles); 0.15 grams of hydrido-carbonyl-tris(triphenylphosphine)rhodium (I);4.0 grams of triphenylphosphine and 200 ml of toluene.

The autoclave is sealed and heated to 130° C. while pressurizing same to 500 psig with a 50:50 (mole:mole) mixture of carbon monoxide and hydrogen. The temperature is maintained at 130° C. and the pressure is maintained at 500 psig using additional carbon monoxide and hydrogen for a period of eight hours. At the end of the eight hour period, the autoclave is cooled and the contents are filtered and then distilled through a 2" splash column yielding the following fractions:

| Fraction No. | Vapor Temp. (°C.) | Liquid Temp. (°C.) | Vacuum mm/Hg. Pressure (gms) | Weight of Fraction |
|---|---|---|---|---|
| 1 | 80/92 | 107/103 | 3.4 | 93.0 |
| 2 | 105 | 110 | 3.4 | 46.0 |
| 3 | 110 | 175 | 3.4 | 154.8 |
| 4 | 70 | 210 | 3.4 | 6.1 |

Fractions 2–4 are bulked and redistilled through a 24" Goodloe column.

FIG. 1 is the GLC profile of the crude reaction product prior to distillation.

FIG. 2 is NMR spectrum of the finally distilled material (bulked fractions 3–11) containing the compounds having the structures:

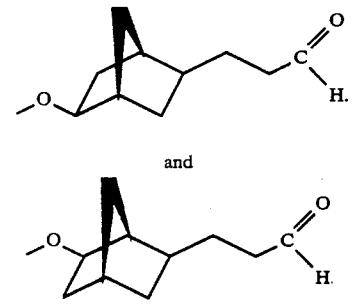

(Conditions: Field strength: 100 MHz; Solvent: CFCl₃).

FIG. 3 is the infra-red spectrum for the mixture of compounds having the structures:

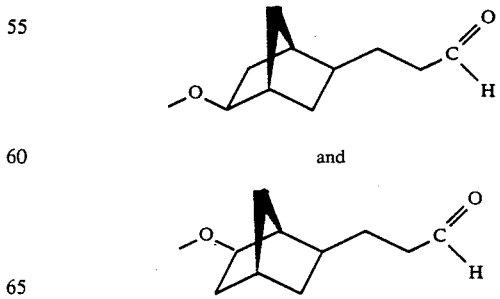

produced according to the foregoing fractional distillation (bulked fractions 3–11).

EXAMPLE II

PREPARATION OF 2-ETHOXY-NORBORNANE-5-PROPANAL

Reaction:

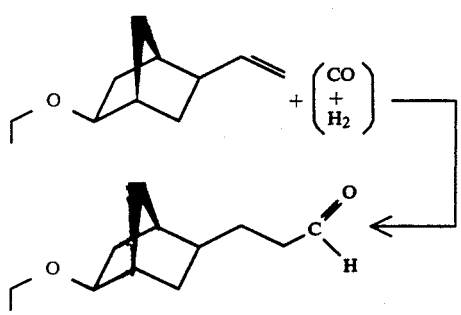

Into a 500 cc autoclave is placed 300 grams of a 60:40 (mole:mole) mixture of ethoxy vinyl norbornanes defined according to the structures:

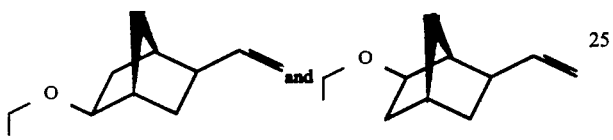

(1.8 moles) 0.15 grams of hydrido-carbonyl-tris(triphenylphosphine)rhodium (I); 5.0 grams of triphenylphosphine and 100 ml of toluene.

The autoclave is sealed and the contents are heated to 130° C. and pressurized to 500 psig using a 50:50 (mole:mole) mixture of carbon monoxide and hydrogen. The reaction mass is maintained at 130° C. and 500 psig using additional carbon monoxide and hydrogen for a period of seven hours. At the end of the seven hour period, the autoclave is cooled and opened. The contents are filtered and then distilled through a 2" splash column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 99/96 | 68/75 | 3.0 | 15.5 |
| 2 | 93 | 104 | 3.0 | 24.1 |
| 3 | 96 | 104 | 2.6 | 24.8 |
| 4 | 109 | 113 | 3.1 | 58.4 |
| 5 | 105 | 114 | 3.1 | 28.2 |
| 6 | 122 | 146 | 3.1 | 159.3 |
| 7 | 134 | 195 | 6.0 | 8.9 |

Fractions 3–7 are bulked and redistilled on a spinning band column yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 62/ | 120/ | 4.0 | 9.4 |
| 2 | 94 | 118 | 2.0 | 16.2 |
| 3 | 100 | 122 | 4.0 | 25.3 |
| 4 | 100 | 124 | 3.0 | 33.9 |
| 5 | 106 | 127 | 4.0 | 26.1 |
| 6 | 105 | 128 | 4.0 | 42.9 |
| 7 | 102 | 131 | 3.0 | 19.9 |
| 8 | 103 | 147 | 0.5 | 22.4 |
| 9 | 38 | 240 | 0.3 | 19.2 |

FIG. 4 is the GLC profile of the crude reaction product prior to the first distillation. The crude reaction product contains the compounds having the structures:

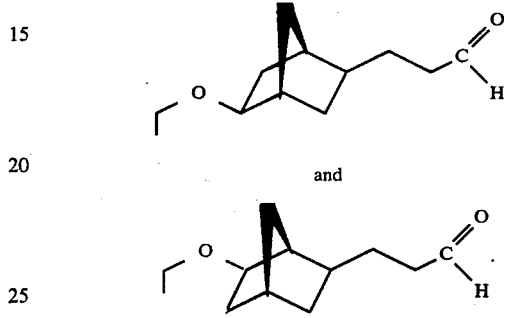

and

FIG. 5 is the NMR spectrum for Fraction 8 of the second distillation containing the compounds having the structures:

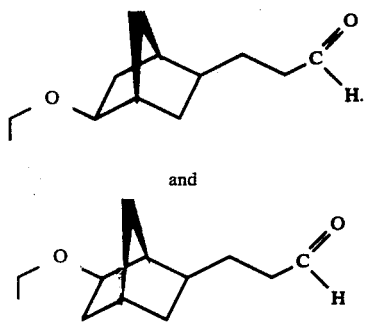

and

FIG. 6 is the infra-red spectrum for Fraction 8 of the second distillation containing the compounds having the structures:

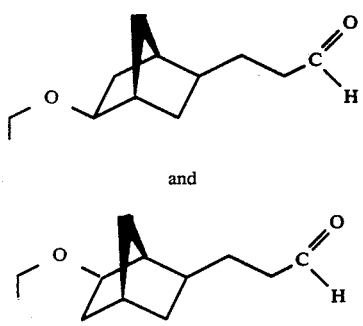

and

EXAMPLE III

PREPARATION OF 5-(1-METHYLETHOXY)BICYCLO[2.2.1]HEPTANE-2-PROPANAL

Reaction:

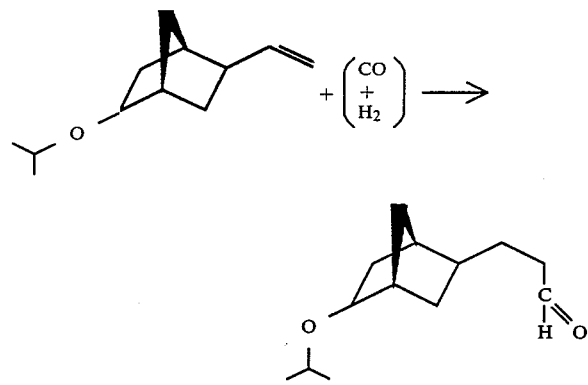

Into a 2-liter autoclave is placed the following ingredients:

(i) 200 grams of a 60:40 mole:mole mixture of isoproproxy vinyl norbornene having the structures, respectively,

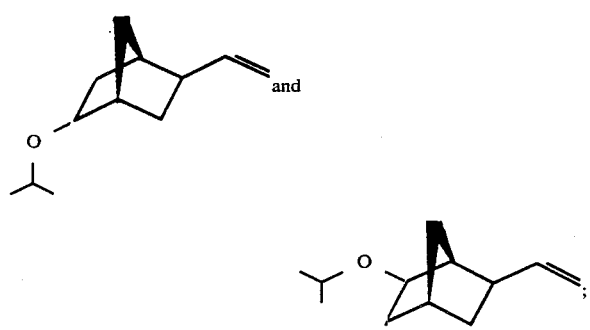

(ii) Rhodium chloride-monocarbonyl-di(triphenylphosphine)-0.2 grams;
(iii) Triphenylphosphine-2.0 grams; and
(iv) Toluene-50 ml.

The autoclave is sealed and heated to 140° C. while simultaneously pressurizing the contents to 500 psig using a 50:50 mole:mole mixture of carbon monoxide and hydrogen. The temperature of the reaction mass is maintained at 140°–150° C. and the pressure is maintained at 500–700 psig using the mixture of carbon monoxide and hydrogen over a period of ten hours. At the end of the ten hour period, the autoclave is cooled and is opened. The contents of the autoclave are filtered and distilled on a 2" splash column yielding the following fractions:

| Fraction No. | Vapor Temp. (°C.) | Liquid Temp. (°C.) | Vacuum mm/Hg. Pressure (gms) | Weight of Fraction |
|---|---|---|---|---|
| 1 | 65/ | 92/ | 8.0 | 74.3 |
| 2 | 84 | 98 | 1.0 | 52.9 |
| 3 | 102 | 120 | 5.0 | 68.4 |
| 4 | 119 | 133 | 5.0 | 7.0 |
| 5 | 114 | 190 | 4.2 | 63.2 |
| 6 | 142 | 250 | 7.0 | 6.6 |

Fractions 2–6 are bulked and the resulting mixture is then redistilled on a spinning band column yielding the following fractions:

| Fraction No. | Vapor Temp. (°C.) | Liquid Temp. (°C.) | Vacuum mm/Hg. Pressure (gms) |
|---|---|---|---|
| 1 | 52/ | 93/ | 2.4 |
| 2 | 74 | 103 | 6.0 |
| 3 | 74 | 104 | 6.0 |
| 4 | 66 | 107 | 3.6 |
| 5 | 66 | 111 | 3.8 |
| 6 | 88 | 118 | 4.2 |
| 7 | 98 | 127 | 4.4 |
| 8 | 100 | 140 | 2.6 |
| 9 | 104 | 155 | 2.6 |
| 10 | 40 | 189 | 4.0 |

FIG. 7 is the GLC profile of the crude reaction product prior to distillation containing the compounds having the structures:

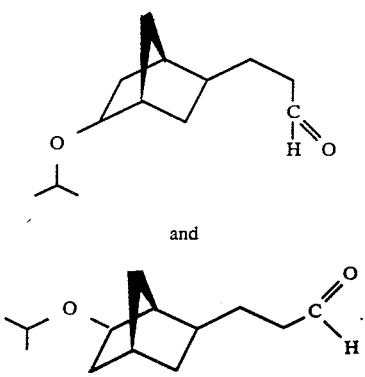

FIG. 8 is the GLC profile for Fraction 8 of the second distillation, supra, containing the compounds having the structures:

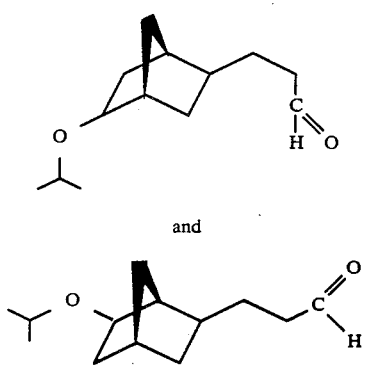

FIG. 9 is the GLC profile for Fraction 10 of the second distillation containing the compound having the structure:

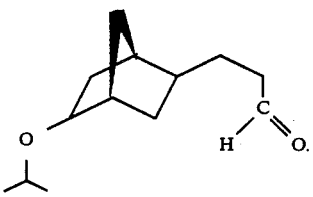

FIG. 10 is the NMR spectrum for Fraction 10 of the second distillation containing the compound having the structure:

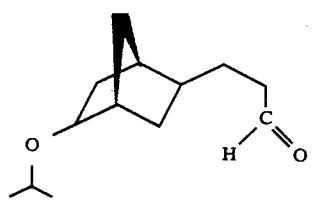

(conditions: Field strength: 100 MHz; Solvent: CFCl₃).

EXAMPLE IV

PREPARATION OF 5-(1-METHYLETHOXY)BICYCLO[2.2.1]HEPTANE-2-PROPANOL

Reaction:

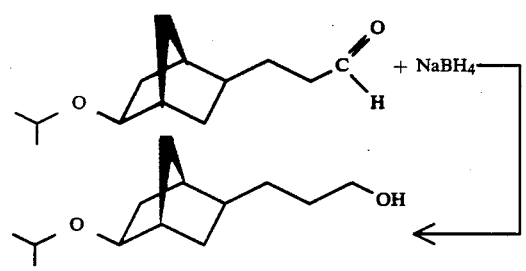

Into a 250 cc reaction flash equipped with stirrer, thermometer, reflux condensor and heating mantle is placed 28.7 grams (0.13 moles) of the reaction product of Example III containing the compounds having the structures:

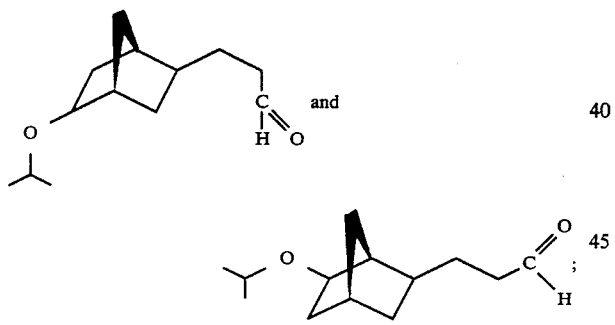

9.6 grams (0.26 moles) of sodium borohydride and 50 ml of anhydrous isopropanol. The isopropanol and sodium borohydride are first mixed together and placed in the flask. The resulting composition is heated to reflux and then over a period of one hour the isopropoxinene norbornane propanal is added. The resulting reaction mass is refluxed for a period of three hours. The reaction mass is then washed to neutral and distilled on a micro vigreux column yielding the following fractions:

| Fraction No. | Vapor Temp. (°C.) | Liquid Temp. (°C.) | Vacuum mm/Hg. Pressure (gms) |
| --- | --- | --- | --- |
| 1 | 34/ | 121/ | 2.2 |
| 2 | 75 | 125 | 1.8 |
| 3 | 93 | 125 | 1.5 |
| 4 | 95 | 128 | 1.8 |
| 5 | 89 | 141 | 1.8 |
| 6 | 80 | 170 | 1.8 |

FIG. 11 is the GLC profile for the crude reaction product prior to distillation containing the compounds having the structures:

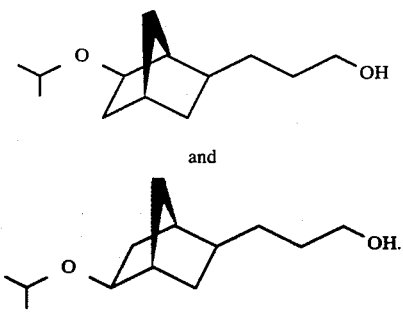

FIG. 12 is the GLC profile for Fraction 5 of the foregoing distillation containing the compounds having the structures:

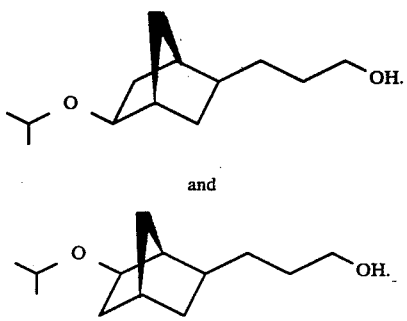

FIG. 13 is the NMR spectrum for Fraction 6 of the foregoing distillation containing the compounds having the structures:

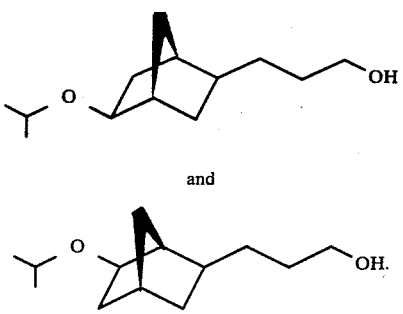

EXAMPLE V

PINE FRAGRANCE

The following pine fragrance formulations are prepared:

| Ingredients | Parts by Weight | | | |
| --- | --- | --- | --- | --- |
| | V-A | V-B | V-C | V-D |
| Isobornyl acetate | 100 | 100 | 100 | 100 |

-continued

| Ingredients | Parts by Weight | | | |
|---|---|---|---|---|
| | V-A | V-B | V-C | V-D |
| Camphor | 10 | 10 | 10 | 10 |
| Terpineol | 25 | 25 | 25 | 25 |
| Fir balsam absolute (50% in diethyl phthalate) | 20 | 20 | 20 | 20 |
| Coumarin | 4 | 4 | 4 | 4 |
| Linalool | 30 | 30 | 30 | 30 |
| Frenchyl alcohol | 10 | 10 | 10 | 10 |
| Anethol | 12 | 12 | 12 | 12 |
| Lemon terpenes washed | 50 | 50 | 50 | 50 |
| Borneol | 5 | 5 | 5 | 5 |
| Galbanum oil | 5 | 5 | 5 | 5 |
| Turpentine Russian | 150 | 150 | 150 | 150 |
| Eucalyptol | 50 | 50 | 50 | 50 |
| 2,2,6-trimethyl-1-cyclohexene-1-carboxaldehyde | 12 | 12 | 12 | 12 |
| Maltol (1% in diethyl phthalate) | 5 | 5 | 5 | 5 |
| The mixture of compounds having the structures: | 28 | 0 | 0 | 0 |

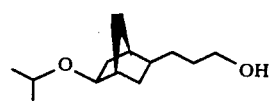

and

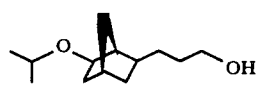

prepared according to Example IV.

| The mixture of compounds having the structures: | 0 | 28 | 0 | 0 |

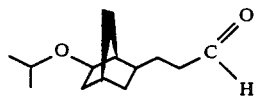

and

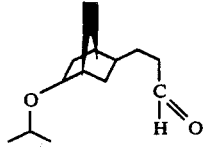

prepared according to Example III.

| The mixture of compounds having the structures: | 0 | 0 | 28 | 0 |

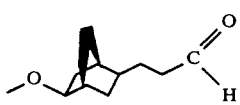

and

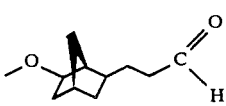

prepared according to Example I.

| The mixture of compounds having the structures: | 0 | 0 | 0 | 28 |

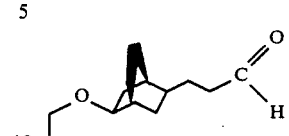

and

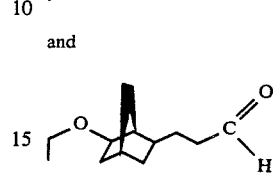

prepared according to Example II.

The mixture of compounds defined according to the structures

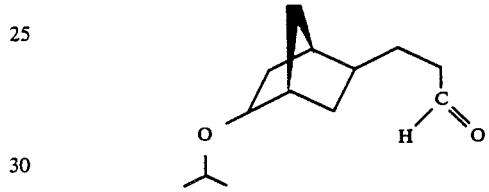

and

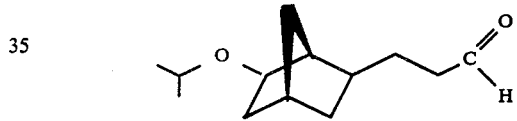

prepared according to Example III imparts to the pine formulation an intense diffusive balsamic nuance. Accordingly, the pine formulation can be described as "piney with an intense diffusive balsamic undertone".

The mixture of compounds defined according to the structures:

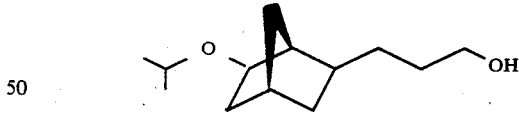

and

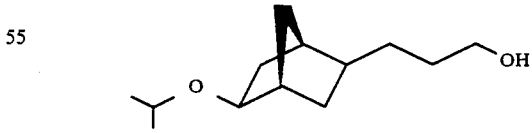

prepared according to Example IV imparts to the pine formulation an intense, balsamic, cedarwood, citrus-like and floral-like aroma profile. The resulting pine formulation can be described as piney with an intense balsamic, cedarwood, citrus-like, green, fruity, melony, orris-like and floral undertones.

The mixtures of compounds defined according to the structures:

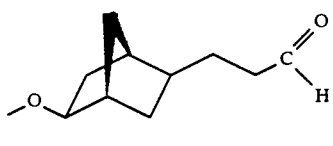

and

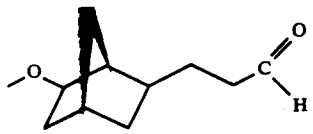

prepared according to Example I imparts to this pine formulation a green, orris, twiggy, melony undertone. Accordingly, the aroma of the formulation can be described as "piney with green, orris and melony, twiggy undertones". The mixtures of compounds defined according to the structures:

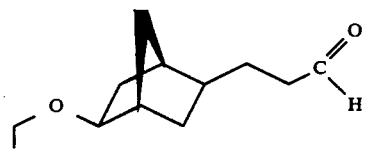

and

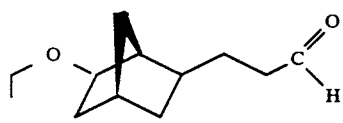

prepared according to Example II imparts to this pine formulation a green, fruity, melony and woody undertone. Accordingly, the resulting formulation can be described as "piney with green, fruity, melony and woody undertones".

EXAMPLE VI

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| Perfume composition of Example V(A). | A piney aroma with an intense balsamic, cedarwood, citrus and floral undertones. |
| Perfume composition of Example V(B). | A piney aroma with an intense and diffusive balsamic undertones. |
| Mixture of chemicals having the structures: 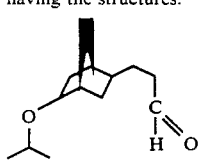 and | An intense diffusive balsamic aroma. |

TABLE II-continued

| Substance | Aroma Description |
|---|---|
| prepared according to Example III. Mixture of chemicals having the structures: and produced according to Example IV. | An intense, balsamic, cedarwood, citrus-like and floral aroma. |
| Perfume formulation produced according to Example V-C. | A pine aroma with green, orris, melony and twiggy undertones. |
| Perfume formulation produced according to Example V-D. | A piney aroma with green, fruity, melony and woody undertones. |
| Mixture of compounds having the structures defined thusly: and | A green, aldehydic, fatty, orris aroma with melony, and twiggy undertones. |
| Mixture of compounds having the structures: and | A green, fruity, melony, aldehydic and woody aroma profile. |

EXAMPLE VII

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table II of Example VI are prepared containing 0.10%, 0.15%, 0.20%, 0.25%, 0.30% and 0.35% of the substance set forth in Table II of Example VI. They are prepared by adding and homogeneously mixing the appropriate quantity of substance set forth in Table II of Example VI in the liquid detergent. The detergents all possess excellent aromas as set forth in Table II of Example VI, the intensity increasing with greater concentrations of substance as set forth in Table II of Example VI.

EXAMPLE VIII

PREPARATION OF COLOGNES AND HANDKERCHIEF PERFUMES

Compositions as set forth in Table II of Example VI are incorporated into colognes at concentrations of 2.0%, 2.5%, 3.0%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VI are imparted to the colognes and to the handkerchief perfumes at all levels indicated.

EXAMPLE IX

PREPARATION OF SOAP COMPOSITIONS

One hundred grams of soap chips (per sample) (IVORY ®, produced by the Procter & Gamble Company of Cincinnati, Ohio), are each mixed with one gram samples of substances as set forth in Table II of Example VI until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VI.

EXAMPLE X

PREPARATION OF SOLID DETERGENT COMPOSITIONS

Detergents are prepared using the following ingredients according to Example I of Canadian Pat. No. 1,007,948 (incorporated herein by reference):

| Ingredient | Percent by Weight |
| --- | --- |
| Neodol ® 45-11 (a $C_{14}$—$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

The detergent is a phosphate-free detergent. Samples of 100 grams each of this detergent are admixed with 0.10, 0.15, 0.20 and 0.25 grams of each of the substances as set forth in Table II of Example VI. Each of the detergent samples has an excellent aroma as indicated in Table II of Example VI.

EXAMPLE XI

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfuming material are as follows:
 1. A water "dissolvable" paper ("Dissolvo Paper")
 2. Adogen 448 (m.p. about 140° F.) as the substrate coating; and
 3. An outer coating having the following formulation (m.p. about 150° F.):
   57% $C_{20-22}$ HAPS
   22% isopropyl alcohol
   20% antistatic agent
   1% of one of the substances as set forth in Table II of Example VI.

Fabric softening compositions prepared according to Example I at column 15 of U.S. Pat. No. 3,632,396 having aroma characteristics as set forth in Table II of Example VI, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example VI is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example VI, supra.

EXAMPLE XII

HAIR SPRAY FORMULATIONS

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example VI, supra. | 0.10 |

The perfume substances as set forth in Table II of Example VI add aroma characteristics as set forth in Table II of Example VI which are rather intense and aesthetically pleasing to the users of the soft-feel, good-hold pump hair sprays.

EXAMPLE XIII

CONDITIONING SHAMPOOS

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is COMPOSITION A.

Gafquat ®755 N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is COMPOSITION B.

The resulting COMPOSITION A & COMPOSITION B are then mixed in a 50:50 wt ratio of A:B and cooled to 45° C. and 0.3 wt percent of perfuming substance as set forth in Table II of Example VI is added to the mixture. The resulting mixture is cooled to 40° C. and blending is carried out for an additional one hour in each case. At the end of this blending period, the resulting material has a pleasant fragrance as indicated in Table II of Example VI.

EXAMPLE XIV

Each of the fragrance materials of Table II of Example VI, supra, are added to a 50:50 weight:weight mixture of low density polyethylene: polyepsilon caprolactone PCL-700 forming pellets with scents as set forth in Table II of Example VI, supra.

75 Pounds of a 50:50 mixture of PCL-700 polyepsilon caprolactone (manufactured by the Union Carbide Corporation of New York, N.Y. having a melting point of about 180°–190° F.): Low density polyethylene, are heated to about 250° F. in a container of the kind illustrated in FIGS. 14 and 15. 25 Pounds of each of the fragrance materials as set forth in Table II of Example VI, is then quickly added to the liquified polymer mixture, the lid 228 is put in place and the agitating means 273 are actuated. The temperature is then raised to about 260° F. and the mixing is continued for 5–15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example VI, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example VI, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example VI, supra.

PATENTS INCORPORATED HEREIN BY REFERENCE

The following patents referred to, supra, are hereby incorporated herein by reference:
U.S. Pat. No. 3,505,432
U.S. Pat. No. 4,247,498
U.K. Pat. No. 1,589,201
U.S. Pat. No. 4,374,277
U.S. Pat. No. 4,359,390
U.S. Pat. No. 4,360,682
U.S. Pat. No. 3,632,396
U.S. Pat. No. 3,948,818
Canadian Pat. No. 1,007,948.

What is claimed is:

1. A compound having the structure selected from the group consisting of:

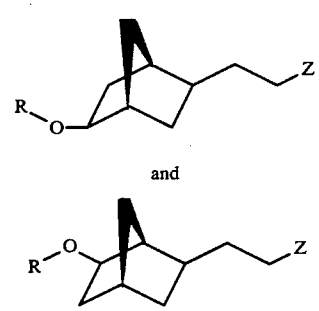

and (wherein R represents $C_1$–$C_3$ alkyl and wherein Z represents one of the moieties, carbinol having the structure:

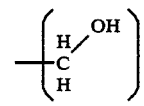

or carboxaldehyde having the structure:

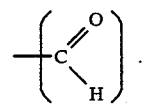

2. A process for augmenting or enhancing the aroma of a consumable material selected from the group consisting of perfume compositions, colognes and perfumed articles comprising the step of adding to said consumable material an aroma augmenting or enhancing quantity of at least one compound defined according to claim 1.

3. The process of claim 2 wherein the consumable material is a perfumed article and the perfumed article is a solid or liquid anionic, cationic, nonionic or zwitterionic detergent.

4. The process of claim 2 wherein the consumable material is a perfumed article and the perfumed article is a perfumed polymer.

5. The process of claim 2 wherein the consumable material is a perfumed composition.

6. The process of claim 2 wherein the consumable material is a cologne.

7. The process of claim 2 wherein the consumable material is a perfumed article and the perfumed article is a fabric softener or drier-added fabric softener article.

8. A product produced according to the process of reacting a compound selected from the group consisting of compounds having the structures:

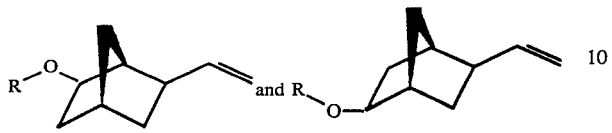

wherein R is $C_1$–$C_3$ alkyl with a mixture of carbon monoxide and hydrogen in the presence of an oxo reaction catalyst.

9. A process for augmenting or enhancing the aroma of a consumable material selected from the group consisting of perfume compositions, colognes and perfumed articles comprising the step of adding to said consumable material an aroma augmenting or enhancing quantity of at least one composition of matter defined according to claim 8.

10. The process of claim 9 wherein the consumable material is a perfume composition.

11. The process of claim 9 wherein the consumable material is a cologne.

12. The process of claim 9 wherein the consumable material is a perfumed article and the perfumed article is a solid or liquid anionic, cationic, nonionic or zwitterionic detergent.

13. The process of claim 9 wherein the consumable material is a perfumed article and the perfumed article is a perfumed polymer.

14. The process of claim 9 wherein the consumable material is a perfumed article and the perfumed article is a fabric softener composition or drier-added fabric softener article.

15. A product produced according to a process which comprises the steps of:
(i) reacting a mixture of carbon monoxide and hydrogen in the presence of an oxo reaction catalyst with at least one compound selected from the group consisting of compounds having the structures:

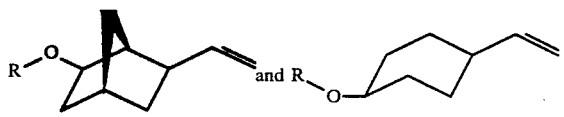

wherein R is $C_1$–$C_3$ lower alkyl thereby producing a mixture of aldehydes defined according to the structures:

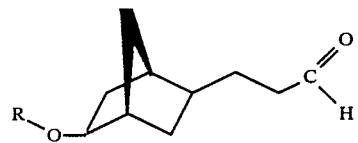
and

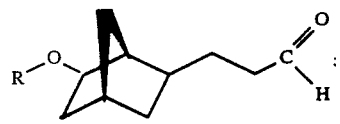

(ii) reducing the resulting mixture of aldehydes defined according to the structures:

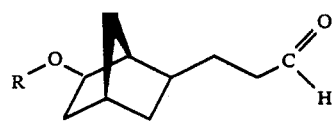

and

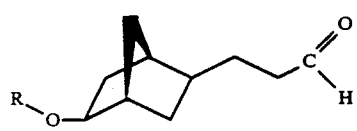

with a reducing agent selected from the group consisting of sodium boro hydride, potassium boro hydride, lithium boro hydride and lithium aluminum hydride thereby producing a mixture of alcohols defined according to the structures:

and

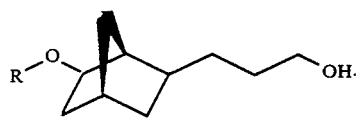

16. A process for augmenting or enhancing the aroma of a consumable material selected from the group consisting of perfume compositions, colognes and perfumed articles comprising the step of intimately admixing with said consumable material an aroma augmenting or enhancing quantity of a product defined according to claim 15.

17. The process of claim 16 wherein the consumable material is a perfumed composition.

18. The process of claim 16 wherein the consumable material is a cologne.

19. The process of claim 16 wherein the consumable material is a perfumed article and the perfumed article is a solid or liquid anionic, cationic, nonionic or zwitterionic detergent.

20. The process of claim 16 wherein the consumable material is a perfumed article and the perfumed article is a perfumed polymer.

21. The process of claim 16 wherein the consumable material is a perfumed article and the perfumed article is a fabric softener composition or drier-added fabric softener article.

* * * * *